US007135281B2

(12) United States Patent
Doorbar

(10) Patent No.: US 7,135,281 B2
(45) Date of Patent: *Nov. 14, 2006

(54) SCREENING FOR PAPILLOMA VIRUSES

(75) Inventor: John Doorbar, London (GB)

(73) Assignee: Medical Research Council, London (GB)

( * ) Notice: Subject to any disclaimer, the term of this patent is extended or adjusted under 35 U.S.C. 154(b) by 331 days.

This patent is subject to a terminal disclaimer.

(21) Appl. No.: 10/008,524

(22) Filed: Nov. 5, 2001

(65) Prior Publication Data

US 2003/0175682 A1 Sep. 18, 2003

Related U.S. Application Data

(63) Continuation of application No. 09/314,268, filed on May 18, 1999, now Pat. No. 6,346,377, which is a continuation of application No. PCT/GB97/03321, filed on Dec. 3, 1997.

(30) Foreign Application Priority Data

Dec. 3, 1996 (GB) .................................. 9625142.6
Sep. 5, 1997 (GB) .................................. 9718745.4

(51) Int. Cl.
*C12Q 1/70* (2006.01)
*G01N 33/574* (2006.01)
(52) U.S. Cl. ............................... 435/5; 435/7.23
(58) Field of Classification Search ............ 435/5, 435/7.23; 530/387.9, 389.4, 388.3
See application file for complete search history.

(56) References Cited

U.S. PATENT DOCUMENTS 5,415,995 A * 5/1995 Schoolnik et al. ........... 435/7.1

6,346,377 B1 * 2/2002 Doorbar ........................ 435/5

FOREIGN PATENT DOCUMENTS

EP 0 451 550 A2 10/1991
WO WO 91 18294 A1 11/1991

OTHER PUBLICATIONS

Palefsky et al, Journal of Clinical Investigation, 87:2132-2141, 1991.*
Doorbar et al, Virology 187: 353-359, 1992.*
Crum et al. Virology 178:238-246 (1990).*
Webster's New World Dictionary, College Edition, 1968, World Publishing Co., Cleveland and New York, pp. 403, 399.*
J. Doorbar et al., *Analysis Of HPV-1 E4 Gene Expression Using Epitope-Defined Antibodies,* The EMBO Journal, vol. 7, No. 3, 1988 Oxford UK, pp. 825-833.
J. Doorbar et al., *Identification Of The Human Papilloma Virus-1a E4 Gene Products,* The EMBO Journal, vol. 5, No. 2, 1986, Oxford UK, pp. 355-362.
J. Doorbar et al., *Characterization Of Events During The Late Stages Of HPV 16 Infection In Vivo Using High-Affinity Synthetic Fabs To E4,* Virology, vol. 238, No. 1, Dec. 1, 1997, New York NY USA, pp. 40-52.
Mark G. Frattini et al., *Induction of Human Papillomavirus Type 18 Late Gene Expression and Genomic Amplification in Organotypic Cultures from Transfected DNA Templates,* American Society for Microbiology, Journal of Virology, Sep. 1997, pp. 7068-7072.
Copy of International Search Report from parent application PCT/GB/03321.

* cited by examiner

*Primary Examiner*—Mary E. Mosher
(74) *Attorney, Agent, or Firm*—Edwards Angell Palmer & Dodge LLP; Kathleen M. Williams

(57) ABSTRACT

The invention relates to a method of screening for precursor lesions which can lead to cervical malignancy, methods of detecting and typing human papilloma virus infections, and reagents of use in these methods.

62 Claims, 10 Drawing Sheets

FIG. 9

```
                                  .... CHARGED REGION ─────┐
most-likely   ..........................................DSDSGEVEG........PTPTTPPAPPTG.....   72
HPV54         ..........................................E-TA.QTSN........H-APQT..........   57
HPV32         ..........................................--LC.SHQQ........S-CS-T.-SQ-Y....   80
HPV42         ..........................................--VDSRHHS........TCS-QT--S-ASP....   81
HPV3          ..........................................N-S-NSNSN........NI-KP--RK-LN.....   67
HPV28         ..........................................S.--............--KP--RK-LN.....   60
HPV10         ..........................................S--K...........G-KI--RR-RN.....   61
HPV29         ..........................................S.T-SSSSNR.......-R--P--RK-VH.....   73
HPV61         ..........................................--TET-SS..........S--QHKKTT-S.....   68
HPV2a         ..........................................S---...SI........-G--LRERSER-.....   79
HPV27         ..........................................S---...SI........SG--LRERSER-.....   76
HPV57         ..........................................S---...S-........NS--LRGRSEK-.....   71
HPV26         ..........................................--VDLTPP..........S-QS-LS-QLPH....   65
HPV30         ..........................................EPQ-PT-O..........--PDS-L-ESPT....   66
HPV53         ..........................................P.Q-PT-L..........TP-HS-LPQ-ES....   63
HPV56         ..........................................-P-Y.GNQN........L--PES-TQSVS.....   62
HPV66         ..........................................-.PEQVNON........L--PES-THTVS.....   62
HPV18         ..........................................-TVD............SRRSS..........   53
HPV45         ..........................................--VD.............SQSST....-D....   55
HPV39         ..........................................--VQ..............SQS-LS--E.....   56
HPV70         ..........................................S.PD............PQKQT..........   51
HPV59         ..........................................--VD.THS..........-LSL-..........   56
HPV7          ..........................................ATHRP-S--........E-E-C-SVQW-DV....   67
HPV40         ..........................................E.TD............-CPS-LLWANHS....   63
HPV16         ..........................................-.Q-QTP-..........--A--LSCC-E.....   50
HPV35h        ..........................................GVP-.............S-----SECDS.....   58
HPV31         ..........................................E.Q-QST-..........------TSCCEA....   64
HPV52         ..........................................Q.T-QTP-..........--S--TTFCGD.....   58
HPV33         ..........................................QTPQ..............--PS-LQSCSV.....   45
HPV58         ..........................................--IYQTP-..........T--S--QSIQ-A.....   49
RhPV1         ..........................................V.GQTQ--..........IQCG-..........   55
HVP6b         ..........................................E.E-....N........SPLA--CVW--L.....   56
HPV11         ..........................................V.-R............PL---CVW--S.....   55
HVP44         ..........................................-PPQ..............-----ET-SVS.....   63
HVP55         ..........................................-PPQ..............-----GT-SVS.....   63
HVP13         ..........................................EDLHVPL-..........--R-HK-LCVS.....   62
PCPV1         ..........................................-.PPTVL-..........NSK--LTLCVP.....   62
HPV34         ..........................................V.TQ..............-RG..........   41
HPV19         ......................................PEERPPPLE-----........HP-PPVTN--GH....  119
HPV25         DPEEKP..............................QPPEGEVQGHPQPPPVT-PQ-........HL-PP-LP--N-HNDRD  149
HPV20         NRRAGGLGTDHD........................PDPEGESPSAPLPPPPPQPPPD-Q---........HP-PP--P-HN-RD..S  144
HPV21         GPIPGPGLNRLTSRNTDSDPEGKCPSSLPPPPPPPPQPTTPPE-OG--........HP-PP--P-NGHDG...  152
HPV14d        LSGGLGTD..................QDPDPDKKKCPESQPPPE-----........HP-PP--NGHNGH...  135
HPV5          .............................GPQPPAE-----HPGG.DQGHP-PP----HN-H....  147
HPV36         ...........................HDPEAPLE-----GGH...GHHP-PP--P---N.....  144
HPV47         ...........................PPVE-----HPQGKDRDHP-P--ONGHGK.....  145
HPV12         ...............................RNPEE-G---........HP--P-LSGGDP....  129
HPV8          DGLQP.........................PLGEGQVEGHPG-GDQPQ-........HP-P--SNGHK-.....  147
HPV24         ...............................V.GETPP-..........GNEESQP--GE.....  120
HPV15         ...............................EGT-ADGD..........D-EK--S--P-E....  106
HPV17         ...............................EGSDASGDEN......A---E--QD----E....  103
HPV37         ...............................EGTDADGDEN......A---E---V----E....  106
HPV9          ...............................-G-E...--..........-P-Q--LP----E....  112
HPV22         ...............................SGEG-PPDD.........-S-EN-QN--G-....   95
HPV23         ...............................NGGG-KPKD..........-P-EE-QN--G-.....   92
HPV38         ...............................P.EAPTG--GTP...GD-P-ED-QS--P-EG..E   99
HPV49         ...............................E-.L-QPP-I.........-A-RE-.-GAE-.....  140
HPV4          ...............................-.-EK-NQ-..........-GQEK---KEEE.....   77
HPV65         ...............................-.--DK-NQ-..........-GQER---KEEE.....   77
HPV48         ...............................-.-DENR-N..........LE-P--.H-ED.....   67
HPV50         ...............................-.EDD-K-N..........TI--DTESHNQN.....   70
HPV60         ...............................-PT-.NK-N..........YP-ESR-V-KDA.....   75
BPV1          ...............................V.GY-T-LA..........R---IF.LQAR-.....   64
BPV2          ...............................V.GY-T-LA..........R---IF.LQAR-.....   63
EEPV          ...............................E.LAKTGV-P.........F-ARL-T-HHHP.....   65
DPV           ...............................VGPL..............-ARL-T-HHSP.....   61
BPV4          ...............................RRGRTP-DE..........TRGYRV-GD-RE.....   71
HPV41         ...............................LT-A...D...........P-RR-N-G-RRRL..F   57
COPV          ...............................---EE-A-N..........YP-SRS.R-RR-R....   69
CRPV          ...............................R.Q-..N-N..........RP-R-K..........   63
ROPV          E......................LDSTQQ-PEDK-NIP........--S-PT-S---P.....   83
HVP1a         ...............................H.LYADGL..........TDGED-EV-EVE.....   69
HPV63         ...............................PT-E...-..........G-EV-EI--SD.....   62
MnPV          ...............................RTP-P-TTA.........QR-KR-RRAC-RK....   81
```

FIG. 9 CONT'D

SEQUENCE LISTING

```
<160> NUMBER OF SEQ ID NOS: 179

<210> SEQ ID NO 1
<211> LENGTH: 375
<212> TYPE: DNA
<213> ORGANISM: Human papillomavirus type 16

<400> SEQUENCE: 1
gcgctgccac tctcagaagt tattgtcaaa aacttgcaac ttgctttggc aaatagctct      60
cgaaatgctg tcgctctttc tgccagccct caactgaaag aggcccagtc agagaaggaa     120 gaagcccaa agccacttca caaagtagtg gtatgtgtta gtaaaaaact cagtaagaag      180
cagagtgaac taaatgggat cgcagcctct ctaggagcag attacaggtg gagttttgat     240
gaaacagtga ctcatttcat ctatcaaggg cggccaaatg acactaatcg ggagtataaa     300
tctgtaaaag aaagaggagt acacattgtt tccgagcact ggcttttaga ttgtgcccaa     360
gagtgtaaac atctt                                                     375

<210> SEQ ID NO 2
<211> LENGTH: 125
```

```
<212> TYPE: PRT
<213> ORGANISM: Homo sapiens

<400> SEQUENCE: 2

Ala Leu Pro Leu Ser Glu Val Ile Val Lys Asn Leu Gln Leu Ala Leu
 1               5                  10                  15

Ala Asn Ser Ser Arg Asn Ala Val Ala Leu Ser Ala Ser Pro Gln Leu
             20                  25                  30

Lys Glu Ala Gln Ser Glu Lys Glu Ala Pro Lys Pro Leu His Lys
         35                  40                  45

Val Val Val Cys Val Ser Lys Lys Leu Ser Lys Gln Ser Glu Leu
     50                  55                  60

Asn Gly Ile Ala Ala Ser Leu Gly Ala Asp Tyr Arg Trp Ser Phe Asp
 65                  70                  75                  80

Glu Thr Val Thr His Phe Ile Tyr Gln Gly Arg Pro Asn Asp Thr Asn
                 85                  90                  95

Arg Glu Tyr Lys Ser Val Lys Glu Arg Gly Val His Ile Val Ser Glu
             100                 105                 110

His Trp Leu Leu Asp Cys Ala Gln Glu Cys Lys His Leu
         115                 120                 125

<210> SEQ ID NO 3
<211> LENGTH: 491
<212> TYPE: PRT
<213> ORGANISM: Homo sapiens

<400> SEQUENCE: 3

Ala Pro Glu Glu His Asp Ser Pro Thr Glu Ala Ser Gln Pro Ile Val
 1               5                  10                  15

Glu Glu Glu Glu Thr Lys Thr Phe Lys Asp Leu Gly Val Thr Asp Val
             20                  25                  30

Leu Cys Glu Ala Cys Asp Gln Leu Gly Trp Thr Lys Pro Thr Lys Ile
         35                  40                  45

Gln Ile Glu Ala Tyr Ser Leu Ala Leu Gln Gly Arg Asp Ile Ile Gly
     50                  55                  60

Leu Ala Glu Thr Gly Ser Gly Lys Thr Gly Ala Phe Ala Leu Pro Ile
 65                  70                  75                  80

Leu Asn Ala Leu Leu Glu Thr Pro Gln Arg Leu Phe Ala Leu Val Leu
                 85                  90                  95

Thr Pro Thr Arg Ser Trp Pro Phe Arg Ser Gln Ser Ser Leu Lys Pro
             100                 105                 110

Trp Ser Ser Ile Gly Val Gln Ser Ala Val Ile Val Gly Gly Ile Asp
         115                 120                 125

Ser Met Ser Gln Ser Leu Ala Leu Ala Lys Lys Pro His Ile Ile Ile
     130                 135                 140

Ala Thr Pro Gly Arg Leu Ile Asp His Leu Glu Asn Thr Lys Gly Phe
145                 150                 155                 160

Asn Leu Arg Ala Leu Lys Tyr Leu Val Met Asp Glu Ala Asp Arg Ile
                 165                 170                 175

Leu Asn Met Asp Phe Glu Thr Glu Val Asp Lys Ile Leu Lys Val Ile
             180                 185                 190

Pro Arg Asp Arg Lys Thr Phe Leu Phe Ser Ala Thr Met Thr Lys Lys
         195                 200                 205

Val Gln Lys Leu Gln Arg Ala Ala Leu Lys Asn Pro Val Lys Cys Ala
     210                 215                 220
```

```
Val Ser Ser Lys Tyr Gln Thr Val Glu Lys Leu Gln Gln Tyr Tyr Ile
225                 230                 235                 240

Phe Ile Pro Ser Lys Phe Lys Asp Thr Tyr Leu Val Tyr Ile Leu Asn
                245                 250                 255

Glu Leu Ala Gly Asn Ser Phe Met Ile Phe Cys Ser Thr Cys Asn Asn
            260                 265                 270

Thr Gln Arg Thr Ala Leu Leu Leu Arg Asn Leu Gly Phe Thr Ala Ile
        275                 280                 285

Pro Leu His Gly Gln Met Ser Lys Arg Leu Gly Ser Leu Asn Lys Phe
    290                 295                 300

Lys Ala Lys Ala Arg Ser Ile Leu Leu Ala Thr Asp Val Ala Ser Arg
305                 310                 315                 320

Gly Leu Asp Ile Pro His Val Asp Val Val Asn Phe Asp Ile Pro
                325                 330                 335

Thr His Ser Lys Asp Tyr Ile His Arg Val Gly Arg Thr Ala Arg Ala
                340                 345                 350

Gly Arg Ser Gly Lys Ala Ile Thr Phe Val Thr Gln Tyr Asp Val Glu
            355                 360                 365

Leu Phe Gln Arg Ile Glu His Leu Ile Gly Lys Lys Leu Pro Gly Phe
        370                 375                 380

Pro Thr Gln Asp Asp Glu Val Met Met Leu Thr Glu Arg Val Ala Glu
385                 390                 395                 400

Ala Gln Arg Phe Ala Arg Met Glu Leu Arg Glu His Gly Glu Lys Lys
                405                 410                 415

Lys Arg Ser Arg Glu Asp Ala Gly Asp Asn Asp Thr Arg Gly Cys
            420                 425                 430

Tyr Val Cys Gln Glu Gln Gly Gly Trp Arg Lys Asn Glu Glu Ala Glu
        435                 440                 445

Arg Pro Leu Ile Thr Phe Met Lys Ala Arg Val Leu Leu Phe Cys Lys
    450                 455                 460

Arg Glu Leu Glu Asn Glu Thr Cys Ser Asn Arg Asp His Glu Thr Glu
465                 470                 475                 480

Ile Gly Gln Asn Cys Val Gln Asn Val Leu Ser
                485                 490

<210> SEQ ID NO 4
<211> LENGTH: 25
<212> TYPE: PRT
<213> ORGANISM: Human papillomavirus type 16

<400> SEQUENCE: 4

Arg Pro Ile Pro Lys Pro Ser Pro Trp Ala Pro Lys Lys His Arg Arg
1               5                   10                  15

Leu Ser Asp Gln Asp Ser Gln Thr Pro
            20                  25

<210> SEQ ID NO 5
<211> LENGTH: 8
<212> TYPE: PRT
<213> ORGANISM: Artificial Sequence
<220> FEATURE:
<223> OTHER INFORMATION: Description of Artificial Sequence: synthetic
      octapeptide antigen

<400> SEQUENCE: 5

Met Ala Asp Pro Ala Ala Ala Thr
1               5
```

```
<210> SEQ ID NO 6
<211> LENGTH: 8
<212> TYPE: PRT
<213> ORGANISM: Artificial Sequence
<220> FEATURE:
<223> OTHER INFORMATION: Description of Artificial Sequence:  synthetic
      octapeptide antigen

<400> SEQUENCE: 6

Ala Asp Pro Ala Ala Ala Thr Lys
  1               5

<210> SEQ ID NO 7
<211> LENGTH: 8
<212> TYPE: PRT
<213> ORGANISM: Artificial Sequence
<220> FEATURE:
<223> OTHER INFORMATION: Description of Artificial Sequence:  synthetic
      octapeptide antigen

<400> SEQUENCE: 7

Asp Pro Ala Ala Ala Thr Lys Tyr
  1               5

<210> SEQ ID NO 8
<211> LENGTH: 8
<212> TYPE: PRT
<213> ORGANISM: Artificial Sequence
<220> FEATURE:
<223> OTHER INFORMATION: Description of Artificial Sequence:  synthetic
      octapeptide antigen

<400> SEQUENCE: 8

Pro Ala Ala Ala Thr Lys Tyr Pro
  1               5

<210> SEQ ID NO 9
<211> LENGTH: 8
<212> TYPE: PRT
<213> ORGANISM: Artificial Sequence
<220> FEATURE:
<223> OTHER INFORMATION: Description of Artificial Sequence:  synthetic
      octapeptide antigen

<400> SEQUENCE: 9

Ala Ala Ala Thr Lys Tyr Pro Leu
  1               5

<210> SEQ ID NO 10
<211> LENGTH: 8
<212> TYPE: PRT
<213> ORGANISM: Artificial Sequence
<220> FEATURE:
<223> OTHER INFORMATION: Description of Artificial Sequence:  synthetic
      octapeptide antigen

<400> SEQUENCE: 10

Ala Ala Thr Lys Tyr Pro Leu Leu
  1               5

<210> SEQ ID NO 11
<211> LENGTH: 8
<212> TYPE: PRT
<213> ORGANISM: Artificial Sequence
<220> FEATURE:
<223> OTHER INFORMATION: Description of Artificial Sequence:  synthetic
      octapeptide antigen
```

```
<400> SEQUENCE: 11

Ala Thr Lys Tyr Pro Leu Leu Lys
 1               5

<210> SEQ ID NO 12
<211> LENGTH: 8
<212> TYPE: PRT
<213> ORGANISM: Artificial Sequence
<220> FEATURE:
<223> OTHER INFORMATION: Description of Artificial Sequence:  synthetic
      octapeptide antigen

<400> SEQUENCE: 12

Thr Lys Tyr Pro Leu Leu Lys Leu
 1               5

<210> SEQ ID NO 13
<211> LENGTH: 8
<212> TYPE: PRT
<213> ORGANISM: Artificial Sequence
<220> FEATURE:
<223> OTHER INFORMATION: Description of Artificial Sequence:  synthetic
      octapeptide antigen

<400> SEQUENCE: 13

Lys Tyr Pro Leu Leu Lys Leu Leu
 1               5

<210> SEQ ID NO 14
<211> LENGTH: 8
<212> TYPE: PRT
<213> ORGANISM: Artificial Sequence
<220> FEATURE:
<223> OTHER INFORMATION: Description of Artificial Sequence:  synthetic
      octapeptide antigen

<400> SEQUENCE: 14

Tyr Pro Leu Leu Lys Leu Leu Gly
 1               5

<210> SEQ ID NO 15
<211> LENGTH: 8
<212> TYPE: PRT
<213> ORGANISM: Artificial Sequence
<220> FEATURE:
<223> OTHER INFORMATION: Description of Artificial Sequence:  synthetic
      octapeptide antigen

<400> SEQUENCE: 15

Pro Leu Leu Lys Leu Leu Gly Ser
 1               5

<210> SEQ ID NO 16
<211> LENGTH: 8
<212> TYPE: PRT
<213> ORGANISM: Artificial Sequence
<220> FEATURE:
<223> OTHER INFORMATION: Description of Artificial Sequence:  synthetic
      octapeptide antigen

<400> SEQUENCE: 16

Leu Leu Lys Leu Leu Gly Ser Thr
 1               5

<210> SEQ ID NO 17
<211> LENGTH: 8
<212> TYPE: PRT
```

```
<213> ORGANISM: Artificial Sequence
<220> FEATURE:
<223> OTHER INFORMATION: Description of Artificial Sequence:  synthetic
      octapeptide antigen

<400> SEQUENCE: 17

Leu Lys Leu Leu Gly Ser Thr Trp
 1               5

<210> SEQ ID NO 18
<211> LENGTH: 8
<212> TYPE: PRT
<213> ORGANISM: Artificial Sequence
<220> FEATURE:
<223> OTHER INFORMATION: Description of Artificial Sequence:  synthetic
      octapeptide antigen

<400> SEQUENCE: 18

Lys Leu Leu Gly Ser Thr Trp Pro
 1               5

<210> SEQ ID NO 19
<211> LENGTH: 8
<212> TYPE: PRT
<213> ORGANISM: Artificial Sequence
<220> FEATURE:
<223> OTHER INFORMATION: Description of Artificial Sequence:  synthetic
      octapeptide antigen

<400> SEQUENCE: 19

Leu Leu Gly Ser Thr Trp Pro Thr
 1               5

<210> SEQ ID NO 20
<211> LENGTH: 8
<212> TYPE: PRT
<213> ORGANISM: Artificial Sequence
<220> FEATURE:
<223> OTHER INFORMATION: Description of Artificial Sequence:  synthetic
      octapeptide antigen

<400> SEQUENCE: 20

Leu Gly Ser Thr Trp Pro Thr Thr
 1               5

<210> SEQ ID NO 21
<211> LENGTH: 8
<212> TYPE: PRT
<213> ORGANISM: Artificial Sequence
<220> FEATURE:
<223> OTHER INFORMATION: Description of Artificial Sequence:  synthetic
      octapeptide antigen

<400> SEQUENCE: 21

Gly Ser Thr Trp Pro Thr Thr Pro
 1               5

<210> SEQ ID NO 22
<211> LENGTH: 8
<212> TYPE: PRT
<213> ORGANISM: Artificial Sequence
<220> FEATURE:
<223> OTHER INFORMATION: Description of Artificial Sequence:  synthetic
      octapeptide antigen

<400> SEQUENCE: 22

Ser Thr Trp Pro Thr Thr Pro Pro
 1               5
```

<210> SEQ ID NO 23
<211> LENGTH: 8
<212> TYPE: PRT
<213> ORGANISM: Artificial Sequence
<220> FEATURE:
<223> OTHER INFORMATION: Description of Artificial Sequence: synthetic octapeptide antigen

<400> SEQUENCE: 23

Thr Trp Pro Thr Thr Pro Pro Arg
 1               5

<210> SEQ ID NO 24
<211> LENGTH: 8
<212> TYPE: PRT
<213> ORGANISM: Artificial Sequence
<220> FEATURE:
<223> OTHER INFORMATION: Description of Artificial Sequence: synthetic octapeptide antigen

<400> SEQUENCE: 24

Trp Pro Thr Thr Pro Pro Arg Pro
 1               5

<210> SEQ ID NO 25
<211> LENGTH: 8
<212> TYPE: PRT
<213> ORGANISM: Artificial Sequence
<220> FEATURE:
<223> OTHER INFORMATION: Description of Artificial Sequence: synthetic octapeptide antigen

<400> SEQUENCE: 25

Pro Thr Thr Pro Pro Arg Pro Ile
 1               5

<210> SEQ ID NO 26
<211> LENGTH: 8
<212> TYPE: PRT
<213> ORGANISM: Artificial Sequence
<220> FEATURE:
<223> OTHER INFORMATION: Description of Artificial Sequence: synthetic octapeptide antigen

<400> SEQUENCE: 26

Thr Thr Pro Pro Arg Pro Ile Pro
 1               5

<210> SEQ ID NO 27
<211> LENGTH: 8
<212> TYPE: PRT
<213> ORGANISM: Artificial Sequence
<220> FEATURE:
<223> OTHER INFORMATION: Description of Artificial Sequence: synthetic octapeptide antigen

<400> SEQUENCE: 27

Thr Pro Pro Arg Pro Ile Pro Lys
 1               5

<210> SEQ ID NO 28
<211> LENGTH: 8
<212> TYPE: PRT
<213> ORGANISM: Artificial Sequence
<220> FEATURE:
<223> OTHER INFORMATION: Description of Artificial Sequence: synthetic octapeptide antigen

```
<400> SEQUENCE: 28

Pro Pro Arg Pro Ile Pro Lys Pro
  1               5

<210> SEQ ID NO 29
<211> LENGTH: 8
<212> TYPE: PRT
<213> ORGANISM: Artificial Sequence
<220> FEATURE:
<223> OTHER INFORMATION: Description of Artificial Sequence: synthetic
      octapeptide antigen

<400> SEQUENCE: 29

Pro Arg Pro Ile Pro Lys Pro Ser
  1               5

<210> SEQ ID NO 30
<211> LENGTH: 8
<212> TYPE: PRT
<213> ORGANISM: Artificial Sequence
<220> FEATURE:
<223> OTHER INFORMATION: Description of Artificial Sequence: synthetic
      octapeptide antigen

<400> SEQUENCE: 30

Arg Pro Ile Pro Lys Pro Ser Pro
  1               5

<210> SEQ ID NO 31
<211> LENGTH: 8
<212> TYPE: PRT
<213> ORGANISM: Artificial Sequence
<220> FEATURE:
<223> OTHER INFORMATION: Description of Artificial Sequence: synthetic
      octapeptide antigen

<400> SEQUENCE: 31

Pro Ile Pro Lys Pro Ser Pro Trp
  1               5

<210> SEQ ID NO 32
<211> LENGTH: 8
<212> TYPE: PRT
<213> ORGANISM: Artificial Sequence
<220> FEATURE:
<223> OTHER INFORMATION: Description of Artificial Sequence: synthetic
      octapeptide antigen

<400> SEQUENCE: 32

Ile Pro Lys Pro Ser Pro Trp Ala
  1               5

<210> SEQ ID NO 33
<211> LENGTH: 8
<212> TYPE: PRT
<213> ORGANISM: Artificial Sequence
<220> FEATURE:
<223> OTHER INFORMATION: Description of Artificial Sequence: synthetic
      octapeptide antigen

<400> SEQUENCE: 33

Pro Lys Pro Ser Pro Trp Ala Pro
  1               5

<210> SEQ ID NO 34
<211> LENGTH: 8
```

```
<212> TYPE: PRT
<213> ORGANISM: Artificial Sequence
<220> FEATURE:
<223> OTHER INFORMATION: Description of Artificial Sequence:  synthetic
      octapeptide antigen

<400> SEQUENCE: 34

Lys Pro Ser Pro Trp Ala Pro Lys
  1               5

<210> SEQ ID NO 35
<211> LENGTH: 8
<212> TYPE: PRT
<213> ORGANISM: Artificial Sequence
<220> FEATURE:
<223> OTHER INFORMATION: Description of Artificial Sequence:  synthetic
      octapeptide antigen

<400> SEQUENCE: 35

Pro Ser Pro Trp Ala Pro Lys Lys
  1               5

<210> SEQ ID NO 36
<211> LENGTH: 8
<212> TYPE: PRT
<213> ORGANISM: Artificial Sequence
<220> FEATURE:
<223> OTHER INFORMATION: Description of Artificial Sequence:  synthetic
      octapeptide antigen

<400> SEQUENCE: 36

Ser Pro Trp Ala Pro Lys Lys His
  1               5

<210> SEQ ID NO 37
<211> LENGTH: 8
<212> TYPE: PRT
<213> ORGANISM: Artificial Sequence
<220> FEATURE:
<223> OTHER INFORMATION: Description of Artificial Sequence:  synthetic
      octapeptide antigen

<400> SEQUENCE: 37

Pro Trp Ala Pro Lys Lys His Arg
  1               5

<210> SEQ ID NO 38
<211> LENGTH: 8
<212> TYPE: PRT
<213> ORGANISM: Artificial Sequence
<220> FEATURE:
<223> OTHER INFORMATION: Description of Artificial Sequence:  synthetic
      octapeptide antigen

<400> SEQUENCE: 38

Trp Ala Pro Lys Lys His Arg Arg
  1               5

<210> SEQ ID NO 39
<211> LENGTH: 8
<212> TYPE: PRT
<213> ORGANISM: Artificial Sequence
<220> FEATURE:
<223> OTHER INFORMATION: Description of Artificial Sequence:  synthetic
      octapeptide antigen

<400> SEQUENCE: 39

Ala Pro Lys Lys His Arg Arg Leu
```

```
<210> SEQ ID NO 40
<211> LENGTH: 8
<212> TYPE: PRT
<213> ORGANISM: Artificial Sequence
<220> FEATURE:
<223> OTHER INFORMATION: Description of Artificial Sequence: synthetic
      octapeptide antigen

<400> SEQUENCE: 40

Pro Lys Lys His Arg Arg Leu Ser
 1               5

<210> SEQ ID NO 41
<211> LENGTH: 8
<212> TYPE: PRT
<213> ORGANISM: Artificial Sequence
<220> FEATURE:
<223> OTHER INFORMATION: Description of Artificial Sequence: synthetic
      octapeptide antigen

<400> SEQUENCE: 41

Lys Lys His Arg Arg Leu Ser Ser
 1               5

<210> SEQ ID NO 42
<211> LENGTH: 8
<212> TYPE: PRT
<213> ORGANISM: Artificial Sequence
<220> FEATURE:
<223> OTHER INFORMATION: Description of Artificial Sequence: synthetic
      octapeptide antigen

<400> SEQUENCE: 42

Lys His Arg Arg Leu Ser Ser Asp
 1               5

<210> SEQ ID NO 43
<211> LENGTH: 8
<212> TYPE: PRT
<213> ORGANISM: Artificial Sequence
<220> FEATURE:
<223> OTHER INFORMATION: Description of Artificial Sequence: synthetic
      octapeptide antigen

<400> SEQUENCE: 43

His Arg Arg Leu Ser Ser Asp Gln
 1               5

<210> SEQ ID NO 44
<211> LENGTH: 8
<212> TYPE: PRT
<213> ORGANISM: Artificial Sequence
<220> FEATURE:
<223> OTHER INFORMATION: Description of Artificial Sequence: synthetic
      octapeptide antigen

<400> SEQUENCE: 44

Arg Arg Leu Ser Ser Asp Gln Asp
 1               5

<210> SEQ ID NO 45
<211> LENGTH: 8
<212> TYPE: PRT
<213> ORGANISM: Artificial Sequence
<220> FEATURE:
<223> OTHER INFORMATION: Description of Artificial Sequence: synthetic
``` octapeptide antigen

<400> SEQUENCE: 45

Arg Leu Ser Ser Asp Gln Asp Gln
 1               5

<210> SEQ ID NO 46
<211> LENGTH: 8
<212> TYPE: PRT
<213> ORGANISM: Artificial Sequence
<220> FEATURE:
<223> OTHER INFORMATION: Description of Artificial Sequence: synthetic
      octapeptide antigen

<400> SEQUENCE: 46

Leu Ser Ser Asp Gln Asp Gln Ser
 1               5

<210> SEQ ID NO 47
<211> LENGTH: 8
<212> TYPE: PRT
<213> ORGANISM: Artificial Sequence
<220> FEATURE:
<223> OTHER INFORMATION: Description of Artificial Sequence: synthetic
      octapeptide antigen

<400> SEQUENCE: 47

Ser Ser Asp Gln Asp Gln Ser Gln
 1               5

<210> SEQ ID NO 48
<211> LENGTH: 8
<212> TYPE: PRT
<213> ORGANISM: Artificial Sequence
<220> FEATURE:
<223> OTHER INFORMATION: Description of Artificial Sequence: synthetic
      octapeptide antigen

<400> SEQUENCE: 48

Ser Asp Gln Asp Gln Ser Gln Thr
 1               5

<210> SEQ ID NO 49
<211> LENGTH: 8
<212> TYPE: PRT
<213> ORGANISM: Artificial Sequence
<220> FEATURE:
<223> OTHER INFORMATION: Description of Artificial Sequence: synthetic
      octapeptide antigen

<400> SEQUENCE: 49

Asp Gln Asp Gln Ser Gln Thr Pro
 1               5

<210> SEQ ID NO 50
<211> LENGTH: 8
<212> TYPE: PRT
<213> ORGANISM: Artificial Sequence
<220> FEATURE:
<223> OTHER INFORMATION: Description of Artificial Sequence: synthetic
      octapeptide antigen

<400> SEQUENCE: 50

Gln Asp Gln Ser Gln Thr Pro Glu
 1               5

<210> SEQ ID NO 51

```
<211> LENGTH: 8
<212> TYPE: PRT
<213> ORGANISM: Artificial Sequence
<220> FEATURE:
<223> OTHER INFORMATION: Description of Artificial Sequence: synthetic
      octapeptide antigen

<400> SEQUENCE: 51

Asp Gln Ser Gln Thr Pro Glu Thr
 1               5

<210> SEQ ID NO 52
<211> LENGTH: 8
<212> TYPE: PRT
<213> ORGANISM: Artificial Sequence
<220> FEATURE:
<223> OTHER INFORMATION: Description of Artificial Sequence: synthetic
      octapeptide antigen

<400> SEQUENCE: 52

Gln Ser Gln Thr Pro Glu Thr Pro
 1               5

<210> SEQ ID NO 53
<211> LENGTH: 8
<212> TYPE: PRT
<213> ORGANISM: Artificial Sequence
<220> FEATURE:
<223> OTHER INFORMATION: Description of Artificial Sequence: synthetic
      octapeptide antigen

<400> SEQUENCE: 53

Ser Gln Thr Pro Glu Thr Pro Ala
 1               5

<210> SEQ ID NO 54
<211> LENGTH: 8
<212> TYPE: PRT
<213> ORGANISM: Artificial Sequence
<220> FEATURE:
<223> OTHER INFORMATION: Description of Artificial Sequence: synthetic
      octapeptide antigen

<400> SEQUENCE: 54

Gln Thr Pro Glu Thr Pro Ala Thr
 1               5

<210> SEQ ID NO 55
<211> LENGTH: 8
<212> TYPE: PRT
<213> ORGANISM: Artificial Sequence
<220> FEATURE:
<223> OTHER INFORMATION: Description of Artificial Sequence: synthetic
      octapeptide antigen

<400> SEQUENCE: 55

Thr Pro Glu Thr Pro Ala Thr Pro
 1               5

<210> SEQ ID NO 56
<211> LENGTH: 8
<212> TYPE: PRT
<213> ORGANISM: Artificial Sequence
<220> FEATURE:
<223> OTHER INFORMATION: Description of Artificial Sequence: synthetic
      octapeptide antigen

<400> SEQUENCE: 56
```

```
Pro Glu Thr Pro Ala Thr Pro Leu
1               5

<210> SEQ ID NO 57
<211> LENGTH: 8
<212> TYPE: PRT
<213> ORGANISM: Artificial Sequence
<220> FEATURE:
<223> OTHER INFORMATION: Description of Artificial Sequence:  synthetic
      octapeptide antigen

<400> SEQUENCE: 57

Glu Thr Pro Ala Thr Pro Leu Ser
1               5

<210> SEQ ID NO 58
<211> LENGTH: 8
<212> TYPE: PRT
<213> ORGANISM: Artificial Sequence
<220> FEATURE:
<223> OTHER INFORMATION: Description of Artificial Sequence:  synthetic
      octapeptide antigen

<400> SEQUENCE: 58

Thr Pro Ala Thr Pro Leu Ser Cys
1               5

<210> SEQ ID NO 59
<211> LENGTH: 8
<212> TYPE: PRT
<213> ORGANISM: Artificial Sequence
<220> FEATURE:
<223> OTHER INFORMATION: Description of Artificial Sequence:  synthetic
      octapeptide antigen

<400> SEQUENCE: 59

Pro Ala Thr Pro Leu Ser Cys Cys
1               5

<210> SEQ ID NO 60
<211> LENGTH: 8
<212> TYPE: PRT
<213> ORGANISM: Artificial Sequence
<220> FEATURE:
<223> OTHER INFORMATION: Description of Artificial Sequence:  synthetic
      octapeptide antigen

<400> SEQUENCE: 60

Ala Thr Pro Leu Ser Cys Cys Thr
1               5

<210> SEQ ID NO 61
<211> LENGTH: 8
<212> TYPE: PRT
<213> ORGANISM: Artificial Sequence
<220> FEATURE:
<223> OTHER INFORMATION: Description of Artificial Sequence:  synthetic
      octapeptide antigen

<400> SEQUENCE: 61

Thr Pro Leu Ser Cys Cys Thr Glu
1               5

<210> SEQ ID NO 62
<211> LENGTH: 8
<212> TYPE: PRT
<213> ORGANISM: Artificial Sequence
<220> FEATURE:
```

```
<223> OTHER INFORMATION: Description of Artificial Sequence:  synthetic
      octapeptide antigen

<400> SEQUENCE: 62

Pro Leu Ser Cys Cys Thr Glu Thr
 1               5

<210> SEQ ID NO 63
<211> LENGTH: 8
<212> TYPE: PRT
<213> ORGANISM: Artificial Sequence
<220> FEATURE:
<223> OTHER INFORMATION: Description of Artificial Sequence:  synthetic
      octapeptide antigen

<400> SEQUENCE: 63

Leu Ser Cys Cys Thr Glu Thr Gln
 1               5

<210> SEQ ID NO 64
<211> LENGTH: 8
<212> TYPE: PRT
<213> ORGANISM: Artificial Sequence
<220> FEATURE:
<223> OTHER INFORMATION: Description of Artificial Sequence:  synthetic
      octapeptide antigen

<400> SEQUENCE: 64

Ser Cys Cys Thr Glu Thr Gln Trp
 1               5

<210> SEQ ID NO 65
<211> LENGTH: 8
<212> TYPE: PRT
<213> ORGANISM: Artificial Sequence
<220> FEATURE:
<223> OTHER INFORMATION: Description of Artificial Sequence:  synthetic
      octapeptide antigen

<400> SEQUENCE: 65

Cys Cys Thr Glu Thr Gln Trp Thr
 1               5

<210> SEQ ID NO 66
<211> LENGTH: 8
<212> TYPE: PRT
<213> ORGANISM: Artificial Sequence
<220> FEATURE:
<223> OTHER INFORMATION: Description of Artificial Sequence:  synthetic
      octapeptide antigen

<400> SEQUENCE: 66

Cys Thr Glu Thr Gln Trp Thr Val
 1               5

<210> SEQ ID NO 67
<211> LENGTH: 8
<212> TYPE: PRT
<213> ORGANISM: Artificial Sequence
<220> FEATURE:
<223> OTHER INFORMATION: Description of Artificial Sequence:  synthetic
      octapeptide antigen

<400> SEQUENCE: 67

Thr Glu Thr Gln Trp Thr Val Leu
 1               5
```

```
<210> SEQ ID NO 68
<211> LENGTH: 8
<212> TYPE: PRT
<213> ORGANISM: Artificial Sequence
<220> FEATURE:
<223> OTHER INFORMATION: Description of Artificial Sequence:  synthetic
      octapeptide antigen

<400> SEQUENCE: 68

Glu Thr Gln Trp Thr Val Leu Gln
  1               5

<210> SEQ ID NO 69
<211> LENGTH: 8
<212> TYPE: PRT
<213> ORGANISM: Artificial Sequence
<220> FEATURE:
<223> OTHER INFORMATION: Description of Artificial Sequence:  synthetic
      octapeptide antigen

<400> SEQUENCE: 69

Thr Gln Trp Thr Val Leu Gln Ser
  1               5

<210> SEQ ID NO 70
<211> LENGTH: 8
<212> TYPE: PRT
<213> ORGANISM: Artificial Sequence
<220> FEATURE:
<223> OTHER INFORMATION: Description of Artificial Sequence:  synthetic
      octapeptide antigen

<400> SEQUENCE: 70

Gln Trp Thr Val Leu Gln Ser Ser
  1               5

<210> SEQ ID NO 71
<211> LENGTH: 8
<212> TYPE: PRT
<213> ORGANISM: Artificial Sequence
<220> FEATURE:
<223> OTHER INFORMATION: Description of Artificial Sequence:  synthetic
      octapeptide antigen

<400> SEQUENCE: 71

Trp Thr Val Leu Gln Ser Ser Leu
  1               5

<210> SEQ ID NO 72
<211> LENGTH: 8
<212> TYPE: PRT
<213> ORGANISM: Artificial Sequence
<220> FEATURE:
<223> OTHER INFORMATION: Description of Artificial Sequence:  synthetic
      octapeptide antigen

<400> SEQUENCE: 72

Thr Val Leu Gln Ser Ser Leu His
  1               5

<210> SEQ ID NO 73
<211> LENGTH: 8
<212> TYPE: PRT
<213> ORGANISM: Artificial Sequence
<220> FEATURE:
<223> OTHER INFORMATION: Description of Artificial Sequence:  synthetic
      octapeptide antigen

<400> SEQUENCE: 73
```

Val Leu Gln Ser Ser Leu His Leu
1               5

<210> SEQ ID NO 74
<211> LENGTH: 8
<212> TYPE: PRT
<213> ORGANISM: Artificial Sequence
<220> FEATURE:
<223> OTHER INFORMATION: Description of Artificial Sequence: synthetic
      octapeptide antigen

<400> SEQUENCE: 74

Leu Gln Ser Ser Leu His Leu Thr
1               5

<210> SEQ ID NO 75
<211> LENGTH: 8
<212> TYPE: PRT
<213> ORGANISM: Artificial Sequence
<220> FEATURE:
<223> OTHER INFORMATION: Description of Artificial Sequence: synthetic
      octapeptide antigen

<400> SEQUENCE: 75

Gln Ser Ser Leu His Leu Thr Ala
1               5

<210> SEQ ID NO 76
<211> LENGTH: 8
<212> TYPE: PRT
<213> ORGANISM: Artificial Sequence
<220> FEATURE:
<223> OTHER INFORMATION: Description of Artificial Sequence: synthetic
      octapeptide antigen

<400> SEQUENCE: 76

Ser Ser Leu His Leu Thr Ala His
1               5

<210> SEQ ID NO 77
<211> LENGTH: 8
<212> TYPE: PRT
<213> ORGANISM: Artificial Sequence
<220> FEATURE:
<223> OTHER INFORMATION: Description of Artificial Sequence: synthetic
      octapeptide antigen

<400> SEQUENCE: 77

Ser Leu His Leu Thr Ala His Thr
1               5

<210> SEQ ID NO 78
<211> LENGTH: 8
<212> TYPE: PRT
<213> ORGANISM: Artificial Sequence
<220> FEATURE:
<223> OTHER INFORMATION: Description of Artificial Sequence: synthetic
      octapeptide antigen

<400> SEQUENCE: 78

His Leu Thr Ala His Thr Lys Asp
1               5

<210> SEQ ID NO 79
<211> LENGTH: 8
<212> TYPE: PRT
<213> ORGANISM: Artificial Sequence

```
<220> FEATURE:
<223> OTHER INFORMATION: Description of Artificial Sequence: synthetic
      octapeptide antigen

<400> SEQUENCE: 79

His Leu Thr Ala His Thr Lys Asp
  1               5

<210> SEQ ID NO 80
<211> LENGTH: 8
<212> TYPE: PRT
<213> ORGANISM: Artificial Sequence
<220> FEATURE:
<223> OTHER INFORMATION: Description of Artificial Sequence: synthetic
      octapeptide antigen

<400> SEQUENCE: 80

Leu Thr Ala His Thr Lys Asp Gly
  1               5

<210> SEQ ID NO 81
<211> LENGTH: 8
<212> TYPE: PRT
<213> ORGANISM: Artificial Sequence
<220> FEATURE:
<223> OTHER INFORMATION: Description of Artificial Sequence: synthetic
      octapeptide antigen

<400> SEQUENCE: 81

Thr Ala His Thr Lys Asp Gly Leu
  1               5

<210> SEQ ID NO 82
<211> LENGTH: 8
<212> TYPE: PRT
<213> ORGANISM: Artificial Sequence
<220> FEATURE:
<223> OTHER INFORMATION: Description of Artificial Sequence: synthetic
      octapeptide antigen

<400> SEQUENCE: 82

Ala His Thr Lys Asp Gly Leu Thr
  1               5

<210> SEQ ID NO 83
<211> LENGTH: 8
<212> TYPE: PRT
<213> ORGANISM: Artificial Sequence
<220> FEATURE:
<223> OTHER INFORMATION: Description of Artificial Sequence: synthetic
      octapeptide antigen

<400> SEQUENCE: 83

His Thr Lys Asp Gly Leu Thr Val
  1               5

<210> SEQ ID NO 84
<211> LENGTH: 8
<212> TYPE: PRT
<213> ORGANISM: Artificial Sequence
<220> FEATURE:
<223> OTHER INFORMATION: Description of Artificial Sequence: synthetic
      octapeptide antigen

<400> SEQUENCE: 84

Thr Lys Asp Gly Leu Thr Val Ile
  1               5
```

```
<210> SEQ ID NO 85
<211> LENGTH: 8
<212> TYPE: PRT
<213> ORGANISM: Artificial Sequence
<220> FEATURE:
<223> OTHER INFORMATION: Description of Artificial Sequence: synthetic
      octapeptide antigen

<400> SEQUENCE: 85

Lys Asp Gly Leu Thr Val Ile Val
 1               5

<210> SEQ ID NO 86
<211> LENGTH: 8
<212> TYPE: PRT
<213> ORGANISM: Artificial Sequence
<220> FEATURE:
<223> OTHER INFORMATION: Description of Artificial Sequence: synthetic
      octapeptide antigen

<400> SEQUENCE: 86

Asp Gly Leu Thr Val Ile Val Thr
 1               5

<210> SEQ ID NO 87
<211> LENGTH: 8
<212> TYPE: PRT
<213> ORGANISM: Artificial Sequence
<220> FEATURE:
<223> OTHER INFORMATION: Description of Artificial Sequence: synthetic
      octapeptide antigen

<400> SEQUENCE: 87

Gly Leu Thr Val Ile Val Thr Leu
 1               5

<210> SEQ ID NO 88
<211> LENGTH: 8
<212> TYPE: PRT
<213> ORGANISM: Artificial Sequence
<220> FEATURE:
<223> OTHER INFORMATION: Description of Artificial Sequence: synthetic
      octapeptide antigen

<400> SEQUENCE: 88

Leu Thr Val Ile Val Thr Leu His
 1               5

<210> SEQ ID NO 89
<211> LENGTH: 8
<212> TYPE: PRT
<213> ORGANISM: Artificial Sequence
<220> FEATURE:
<223> OTHER INFORMATION: Description of Artificial Sequence: synthetic
      octapeptide antigen

<400> SEQUENCE: 89

Thr Val Ile Val Thr Leu His Pro
 1               5

<210> SEQ ID NO 90
<211> LENGTH: 92
<212> TYPE: PRT
<213> ORGANISM: Human papillomavirus type 16

<400> SEQUENCE: 90

Met Ala Asp Pro Ala Ala Ala Thr Lys Tyr Pro Leu Leu Lys Leu Leu
```

```
                 1               5              10              15
Gly Ser Thr Trp Pro Thr Thr Pro Pro Arg Pro Ile Pro Lys Pro Ser
                        20                  25                  30

Pro Trp Ala Pro Lys Lys His Arg Arg Leu Ser Ser Asp Gln Asp Gln
                35                  40                  45

Ser Gln Thr Pro Glu Thr Pro Ala Thr Pro Leu Ser Cys Cys Thr Glu
        50                  55                  60

Thr Gln Trp Thr Val Leu Gln Ser Ser Leu His Leu Thr Ala His Thr
65                  70                  75                  80

Lys Asp Gly Leu Thr Val Ile Val Thr Leu His Pro
                85                  90
```

<210> SEQ ID NO 91
<211> LENGTH: 126
<212> TYPE: PRT
<213> ORGANISM: Human papillomavirus

<400> SEQUENCE: 91

```
Met Ala Asp Asn Lys Ala Pro Gln Gly Leu Leu Gly Leu Leu Gln Tyr
1               5                  10                  15

Thr Pro Thr Thr Gln Pro Tyr Pro Arg Val Thr Pro Ser Asn Arg
                20                  25                  30

Arg Pro Ser Thr Thr Pro Asn Ser Gln Asp Arg Gly Arg Pro Arg Arg
                35                  40                  45

Ser Asp Lys Asp Ser Arg Lys His Leu Tyr Ala Asp Gly Leu Thr Asp
        50                  55                  60

Gly Glu Asp Pro Glu Val Pro Glu Val Glu Asp Glu Lys Glu Asn
65                  70                  75                  80

Gln Arg Pro Leu Gly His Pro Asp Leu Ser Leu Leu Arg Glu Thr Leu
                85                  90                  95

Glu Val Tyr Thr Gln Arg Leu Lys Arg Asp Ile Leu Gln Gln Asp Leu
                100                 105                 110

Asp Asp Phe Cys Arg Lys Leu Gly Ile His Pro Trp Ser Val
        115                 120                 125
```

<210> SEQ ID NO 92
<211> LENGTH: 117
<212> TYPE: PRT
<213> ORGANISM: Artificial Sequence
<220> FEATURE:
<223> OTHER INFORMATION: Description of Artificial Sequence:HPV E4
      Consensus Amino Acid Sequence

<400> SEQUENCE: 92

```
Met Ala Asp Ala Pro Thr Gln Tyr Pro Leu Leu Lys Leu Leu Pro Pro
1               5                  10                  15

Thr Pro Thr Pro Pro Arg Pro Pro Pro Pro Pro Pro Pro Arg
                20                  25                  30

Pro Trp Ala Gly Pro Lys Lys Pro Thr Arg Gly Pro Arg Arg Arg
                35                  40                  45

Arg Leu Glu Ser Asp Ser Asp Ser Gly Glu Val Glu Pro Thr Pro
        50                  55                  60

Thr Thr Pro Pro Ala Pro Pro Thr Gly Asp Glu Glu Val Glu Pro Pro
65                  70                  75                  80

Trp Thr Val Gln Thr Leu Leu Ser Ser Val Thr Leu Thr Trp Glu Tyr
                85                  90                  95

Thr Phe Asp Gly Leu Val Val Ile Val Gln Asp Leu Glu Asp Tyr Trp
```

```
                   100                 105                 110

Lys Lys Leu His Leu
        115

<210> SEQ ID NO 93
<211> LENGTH: 49
<212> TYPE: PRT
<213> ORGANISM: Artificial Sequence
<220> FEATURE:
<223> OTHER INFORMATION: Description of Artificial Sequence: HPV E4
      protein consenus amino acid sequence, amino acids 27-73.

<400> SEQUENCE: 93

Pro Pro Pro Pro Pro Arg Pro Trp Ala Gly Pro Lys Lys Pro Thr Arg
  1               5                  10                  15

Gly Pro Pro Arg Arg Arg Arg Leu Glu Ser Asp Ser Asp Ser Asp Ser
             20                  25                  30

Gly Glu Val Glu Gly Pro Thr Pro Thr Thr Pro Pro Ala Pro Pro Thr
         35                  40                  45

Gly

<210> SEQ ID NO 94
<211> LENGTH: 35
<212> TYPE: PRT
<213> ORGANISM: Human papillomavirus type 54

<400> SEQUENCE: 94

His His Val Pro Thr Thr Pro Gln Lys Gln Ser Arg Ala Arg Arg Arg
  1               5                  10                  15

Leu Glu Asn Glu Leu Glu Ser Thr Ala Gln Thr Ser Asn His Thr Ala
             20                  25                  30

Pro Gln Thr
        35

<210> SEQ ID NO 95
<211> LENGTH: 48
<212> TYPE: PRT
<213> ORGANISM: Human papillomavirus type 32

<400> SEQUENCE: 95

Pro Ser Gln Gly Val Thr Ala Thr Thr Ala Gln Thr Glu Tyr Tyr Thr
  1               5                  10                  15

Lys Thr Pro Pro Arg Pro Pro Arg Arg Glu Asn Asp Thr Asp Ser Leu
             20                  25                  30

Cys Ser His Gln Gln Ser Thr Cys Ser Thr Thr Ala Ser Gln Thr Tyr
         35                  40                  45

<210> SEQ ID NO 96
<211> LENGTH: 50
<212> TYPE: PRT
<213> ORGANISM: Human papillomavirus type 42

<400> SEQUENCE: 96

Pro Leu Thr Thr Thr Thr Gln Thr Val Gln Thr Glu Gln His Thr Thr
  1               5                  10                  15

Cys Pro Ser Lys Pro His Arg His Glu Asn Asp Thr Asp Ser Val Asp
             20                  25                  30

Ser Arg His His Ser Thr Cys Ser Thr Gln Thr Pro Ala Ser Pro Ala
         35                  40                  45

Ser Pro
```

<210> SEQ ID NO 97
<211> LENGTH: 47
<212> TYPE: PRT
<213> ORGANISM: Human papillomavirus type 3

<400> SEQUENCE: 97

Lys Pro Arg Trp Ala Arg Pro Lys Asp Arg Ser Lys Ser Asp Ser Asp
 1               5                  10                  15

Ser Arg Arg Ser Thr Gly Ser Ser Ser Asn Ser Ser Ser Asn Ser
            20                  25                  30

Asn Ser Asn Asn Ile Pro Lys Pro Pro Arg Lys Pro Leu Asn
        35                  40                  45

<210> SEQ ID NO 98
<211> LENGTH: 39
<212> TYPE: PRT
<213> ORGANISM: Human papillomavirus type 28

<400> SEQUENCE: 98

Lys Pro Arg Trp Ala Arg Pro Lys Asp Arg Ser Lys Asn Asp Ser Asp
 1               5                  10                  15

Ser Arg His Ser Thr Gly Ser Ser Ser Ser Asp Ser Thr Pro Lys Pro
            20                  25                  30

Pro Pro Arg Lys Pro Leu Asn
        35

<210> SEQ ID NO 99
<211> LENGTH: 40
<212> TYPE: PRT
<213> ORGANISM: Human papillomavirus type 10

<400> SEQUENCE: 99

Lys Pro Arg Trp Ala Arg Pro Arg Asp Arg Asn Lys Ser Asp Ser Asp
 1               5                  10                  15

Ser Arg Arg Ser Thr Asp Ser Thr Ser Ser Ser Asp Lys Gly Pro Lys
            20                  25                  30

Ile Pro Pro Arg Arg Pro Arg Asn
        35                  40

<210> SEQ ID NO 100
<211> LENGTH: 51
<212> TYPE: PRT
<213> ORGANISM: Human papillomavirus type 29

<400> SEQUENCE: 100

Lys Pro Arg Trp Gly Leu Arg Arg Asp Arg Asn Gly Asn Asp Ala Gly
 1               5                  10                  15

Leu Lys Gln Ser Gly Leu Gly His Ser Ser Ser Ser Ser Ser Ser Thr
            20                  25                  30

Ser Ser Ser Ser Ser Asn Arg Pro Arg Pro Thr Pro Pro Pro Arg Lys
        35                  40                  45

Pro Val His
    50

<210> SEQ ID NO 101
<211> LENGTH: 41
<212> TYPE: PRT
<213> ORGANISM: Human papillomavirus type 61

-continued

```
<400> SEQUENCE: 101

Pro Pro Arg Ala Trp Ala Pro Pro Arg His Pro Pro Arg Cys Arg Arg
1               5                   10                  15

Arg Leu Ile Ser Asp Ser Asp Ser Thr Glu Thr Glu Ser Ser Ser Pro
                20                  25                  30

Thr Gln His Lys Lys Thr Thr Thr Ser
            35                  40

<210> SEQ ID NO 102
<211> LENGTH: 45
<212> TYPE: PRT
<213> ORGANISM: Human papillomavirus type 2a

<400> SEQUENCE: 102

Gln Glu Glu Gln Leu Arg Pro Pro Lys Arg Cys Ala Pro Pro Arg Arg
1               5                   10                  15

Gln Arg Val Arg Arg Pro Ser Ala Ser Val Ser Ser Ser Asp Ser Ser
                20                  25                  30

Ile Pro Gly Pro Thr Leu Arg Glu Arg Ser Glu Arg Gly
            35                  40                  45

<210> SEQ ID NO 103
<211> LENGTH: 45
<212> TYPE: PRT
<213> ORGANISM: Human papillomavirus type 27

<400> SEQUENCE: 103

Glu Gln Glu Gln Leu Arg Pro Gln Thr Cys Cys Ala Pro Pro Arg Arg
1               5                   10                  15

His Arg Val Arg Arg Pro Ser Ala Ser Gly Ser Ser Ser Asp Ser Ser
                20                  25                  30

Ile Ser Gly Pro Thr Leu Arg Glu Arg Ser Glu Arg Gly
            35                  40                  45

<210> SEQ ID NO 104
<211> LENGTH: 41
<212> TYPE: PRT
<213> ORGANISM: Human papillomavirus type 57

<400> SEQUENCE: 104

Gln Ser Arg Pro His Ser Arg Thr Pro Pro Arg Arg His Arg Val Arg
1               5                   10                  15

His Pro Ser Ala Ser Gly Ser Ser Ser Asp Ser Ser Gly Asn Ser Pro
                20                  25                  30

Thr Leu Arg Gly Arg Ser Glu Lys Gly
            35                  40

<210> SEQ ID NO 105
<211> LENGTH: 39
<212> TYPE: PRT
<213> ORGANISM: Human papillomavirus type 26

<400> SEQUENCE: 105

Pro Thr Cys Pro Trp Ala Pro Arg Lys Pro Arg Arg His Thr Gln Glu
1               5                   10                  15

Ser Asp Asp Asp Ser Val Asp Leu Thr Pro Ser Pro Gln Ser Pro
                20                  25                  30

Leu Ser Pro Gln Leu Pro His
            35
```

-continued

<210> SEQ ID NO 106
<211> LENGTH: 40
<212> TYPE: PRT
<213> ORGANISM: Human papillomavirus type 30

<400> SEQUENCE: 106

Pro Pro Arg Pro Trp Ala Pro Thr Lys Pro Arg Pro His Gly Arg
 1               5                  10                  15

Glu Asn Val Leu Glu Pro Gln Ser Pro Thr Val Gln Thr Pro Pro Asp
            20                  25                  30

Ser Pro Leu Pro Glu Ser Pro Thr
        35                  40

<210> SEQ ID NO 107
<211> LENGTH: 40
<212> TYPE: PRT
<213> ORGANISM: Human papillomavirus type 53

<400> SEQUENCE: 107

Pro Pro Arg Pro Trp Ala Pro Thr Lys Pro His His Pro Cys Gly Arg
 1               5                  10                  15

Glu Asn Val Pro Glu Pro Gln Ser Pro Thr Val Leu Thr Pro Pro His
            20                  25                  30

Ser Pro Leu Pro Gln Pro Glu Ser
        35                  40

<210> SEQ ID NO 108
<211> LENGTH: 39
<212> TYPE: PRT
<213> ORGANISM: Human papillomavirus type 56

<400> SEQUENCE: 108

Pro Pro Pro Arg Pro Trp Ala Thr Lys Thr Pro Gln Tyr Pro Thr Asp
 1               5                  10                  15

Gln Glu Asn Asp Pro Asp Tyr Gly Asn Gln Asn Leu Thr Pro Pro Glu
            20                  25                  30

Ser Pro Thr Gln Ser Val Ser
        35

<210> SEQ ID NO 109
<211> LENGTH: 37
<212> TYPE: PRT
<213> ORGANISM: Human papillomavirus type 66

<400> SEQUENCE: 109

Pro Pro Leu Trp Ala Pro Lys Thr Pro Arg Tyr Pro Thr Asp Gln Glu
 1               5                  10                  15

Asn Asp Pro Glu Gln Val Asn Gln Asn Leu Thr Pro Glu Ser Pro
            20                  25                  30

Thr His Thr Val Ser
        35

<210> SEQ ID NO 110
<211> LENGTH: 29
<212> TYPE: PRT
<213> ORGANISM: Human papillomavirus type 18

<400> SEQUENCE: 110

Ala Pro Cys Pro Trp Ala Pro Gln Arg Pro Thr Ala Arg Arg Arg Leu
 1               5                  10                  15

-continued

Leu His Asp Leu Asp Thr Val Asp Ser Arg Arg Ser Ser
            20                  25

<210> SEQ ID NO 111
<211> LENGTH: 31
<212> TYPE: PRT
<213> ORGANISM: Human papillomavirus type 45

<400> SEQUENCE: 111

Lys Pro His Pro Trp Ala Pro Gln Asn Pro Thr Ser Arg Arg Arg Leu
 1               5                  10                  15

Leu Ser Asp Leu Asp Ser Val Asp Ser Gln Ser Ser Thr Thr Asp
            20                  25                  30

<210> SEQ ID NO 112
<211> LENGTH: 32
<212> TYPE: PRT
<213> ORGANISM: Human papillomavirus type 39

<400> SEQUENCE: 112

Pro Gln Gln Pro His Ala Pro Lys Lys Gln Ser Arg Arg Arg Leu Glu
 1               5                  10                  15

Ser Asp Leu Asp Ser Val Gln Ser Gln Ser Pro Leu Ser Pro Thr Glu
            20                  25                  30

<210> SEQ ID NO 113
<211> LENGTH: 27
<212> TYPE: PRT
<213> ORGANISM: Human papillomavirus type 70

<400> SEQUENCE: 113

Pro Gln Gln Pro His Ala Pro Lys Lys Leu Ser Arg Arg Arg Leu Ala
 1               5                  10                  15

Ser Val Glu Ser Pro Asp Pro Gln Lys Gln Thr
            20                  25

<210> SEQ ID NO 114
<211> LENGTH: 32
<212> TYPE: PRT
<213> ORGANISM: Human papillomavirus type 59

<400> SEQUENCE: 114

Lys Pro Arg Thr Trp Ala Pro Lys Arg Gly Thr Val Arg Arg Arg Leu
 1               5                  10                  15

Glu Ser Asp Gln Asp Ser Val Asp Thr His Ser Thr Leu Ser Leu Pro
            20                  25                  30

<210> SEQ ID NO 115
<211> LENGTH: 46
<212> TYPE: PRT
<213> ORGANISM: Human papillomavirus type 7

<400> SEQUENCE: 115

Pro Pro Thr Pro Pro Arg Cys Thr Thr Pro Pro Thr Pro Cys Pro Arg
 1               5                  10                  15

Arg Pro Pro Lys Tyr Thr Thr Ala Thr His Arg Pro Glu Ser Glu
            20                  25                  30

Gly Glu Thr Glu Thr Cys Pro Ser Val Gln Trp Thr Asp Val
        35                  40                  45

<210> SEQ ID NO 116
<211> LENGTH: 41

```
<212> TYPE: PRT
<213> ORGANISM: Human papillomavirus type 40

<400> SEQUENCE: 116

Pro Thr Pro Pro Thr Pro Pro Gln Arg Pro Pro Lys Arg Ser Ala
1               5                   10                  15

Pro Pro Arg His Arg Pro Glu Ser Asp Glu Glu Thr Asp Thr Cys Pro
            20                  25                  30

Ser Pro Leu Leu Trp Ala Asn His Ser
        35                  40

<210> SEQ ID NO 117
<211> LENGTH: 35
<212> TYPE: PRT
<213> ORGANISM: Human papillomavirus type 16

<400> SEQUENCE: 117

Lys Pro Ser Pro Trp Ala Pro Lys Lys His Arg Arg Leu Ser Ser Asp
1               5                   10                  15

Gln Asp Gln Ser Gln Thr Pro Glu Thr Pro Ala Thr Pro Leu Ser Cys
            20                  25                  30

Cys Thr Glu
        35

<210> SEQ ID NO 118
<211> LENGTH: 34
<212> TYPE: PRT
<213> ORGANISM: Human papillomavirus type 35

<400> SEQUENCE: 118

Lys Pro Ala Pro Trp Ala Pro Gln Lys Pro Arg Arg Gln Ile Thr Asn
1               5                   10                  15

Asp Phe Glu Gly Val Pro Ser Ser Pro Thr Thr Pro Pro Ser Glu Cys
            20                  25                  30

Asp Ser

<210> SEQ ID NO 119
<211> LENGTH: 39
<212> TYPE: PRT
<213> ORGANISM: Human papillomavirus type 31

<400> SEQUENCE: 119

Lys Pro Ala Pro Trp Ala Pro Val Lys Val Cys Gly Gly Arg Arg Arg
1               5                   10                  15

Leu Leu Ser Asp Gln Glu Gln Ser Gln Ser Thr Glu Thr Pro Thr Thr
            20                  25                  30

Pro Thr Ser Cys Cys Glu Ala
        35

<210> SEQ ID NO 120
<211> LENGTH: 38
<212> TYPE: PRT
<213> ORGANISM: Human papillomavirus type 52

<400> SEQUENCE: 120

Pro Gln Cys Pro Trp Val Pro Lys Thr His Thr Tyr Asn His His Arg
1               5                   10                  15

Asn Asp Asp Asp Gln Thr Ser Gln Thr Pro Glu Thr Pro Ser Thr Pro
            20                  25                  30

Thr Thr Phe Cys Gly Asp
```

-continued

<210> SEQ ID NO 121
<211> LENGTH: 26
<212> TYPE: PRT
<213> ORGANISM: Human papillomavirus type 33

<400> SEQUENCE: 121

His His Lys Gln Arg Pro Asn Asp Asp Leu Gln Thr Pro Gln Thr
1               5                   10                  15

Pro Pro Ser Pro Leu Gln Ser Cys Ser Val
            20                  25

<210> SEQ ID NO 122
<211> LENGTH: 32
<212> TYPE: PRT
<213> ORGANISM: Human papillomavirus type 58

<400> SEQUENCE: 122

Pro Thr Thr Lys Val His Arg Gly Gln Ser Asp Asp Ser Ile Tyr
1               5                   10                  15

Gln Thr Pro Glu Thr Thr Pro Ser Thr Pro Gln Ser Ile Gln Thr Ala
            20                  25                  30

<210> SEQ ID NO 123
<211> LENGTH: 29
<212> TYPE: PRT
<213> ORGANISM: rhesus monkey papillomavirus

<400> SEQUENCE: 123

Pro Thr Pro Ala Pro Arg Lys Thr Cys Gly His Arg Leu Gln Ser Glu
1               5                   10                  15

Cys Val Gly Gln Thr Gln Val Glu Ile Gln Cys Gly Pro
            20                  25

<210> SEQ ID NO 124
<211> LENGTH: 36
<212> TYPE: PRT
<213> ORGANISM: Human papillomavirus type 66

<400> SEQUENCE: 124

Pro Leu Cys Pro Gln Ala Pro Arg Lys Thr Gln Cys Lys Arg Arg Leu
1               5                   10                  15

Gly Asn Glu His Glu Glu Ser Asn Ser Pro Leu Ala Thr Pro Cys Val
            20                  25                  30

Trp Pro Thr Leu
        35

<210> SEQ ID NO 125
<211> LENGTH: 34
<212> TYPE: PRT
<213> ORGANISM: Human papillomavirus type 11

<400> SEQUENCE: 125

Leu Gln Cys Pro Pro Ala Pro Arg Lys Thr Ala Cys Arg Arg Arg Leu
1               5                   10                  15

Gly Ser Glu His Val Asp Arg Pro Leu Thr Thr Pro Cys Val Trp Pro
            20                  25                  30

Thr Ser

<210> SEQ ID NO 126

<211> LENGTH: 40
<212> TYPE: PRT
<213> ORGANISM: Human papillomavirus type 44

<400> SEQUENCE: 126

His Arg Pro His Pro His Cys Pro Leu Ala Pro Pro Arg Thr Ala Trp
1               5                   10                  15
Thr Arg Arg His Val Asn Asp Pro Glu Asp Pro Pro Gln Thr Pro Thr
            20                  25                  30
Thr Pro Glu Thr Pro Ser Val Ser
        35                  40

<210> SEQ ID NO 127
<211> LENGTH: 40
<212> TYPE: PRT
<213> ORGANISM: Human papillomavirus type 55

<400> SEQUENCE: 127

His Arg Pro His Leu His Cys Pro Pro Ala Pro Pro Arg Asn Ala Trp
1               5                   10                  15
Thr Arg Arg His Val Asn Asp Pro Glu Asp Pro Pro Gln Thr Pro Thr
            20                  25                  30
Thr Pro Gly Thr Pro Ser Val Ser
        35                  40

<210> SEQ ID NO 128
<211> LENGTH: 39
<212> TYPE: PRT
<213> ORGANISM: Human papillomavirus type 13

<400> SEQUENCE: 128

Pro Gln Cys Pro Ala Ala Pro Arg Lys Asn Val Cys Lys Arg Arg Leu
1               5                   10                  15
Val Asn Asp Asn Glu Asp Leu His Val Pro Leu Glu Thr Pro Arg Thr
            20                  25                  30
His Lys Ala Leu Cys Val Ser
        35

<210> SEQ ID NO 129
<211> LENGTH: 40
<212> TYPE: PRT
<213> ORGANISM: Pygmy chimpanzee papillomavirus

<400> SEQUENCE: 129

Ala Gln Cys His Pro Ser Pro Gln Lys Ile Val Cys Lys Lys Arg Arg
1               5                   10                  15
Pro Ile Asn Asp Phe Glu Asp Pro Pro Thr Val Leu Glu Asn Ser Lys
            20                  25                  30
Thr Pro Leu Thr Leu Cys Val Pro
        35                  40

<210> SEQ ID NO 130
<211> LENGTH: 22
<212> TYPE: PRT
<213> ORGANISM: Human papillomavirus type 34

<400> SEQUENCE: 130

Ala Thr His Arg Thr Arg Val Cys Gln His Gly Asn Gly Ile Asp Ser
1               5                   10                  15
Val Thr Gln Thr Arg Gly
            20

<210> SEQ ID NO 131
<211> LENGTH: 71
<212> TYPE: PRT
<213> ORGANISM: Human papillomavirus type 19

<400> SEQUENCE: 131

Gly Thr Arg Asp Asp Leu Pro Ala Gly Pro Asp Asp Lys Pro Lys Arg
 1               5                  10                  15

Ala Arg Asn Asp Gln Gly Pro Asn Pro Ser Pro Gly Arg Gly Arg Gly
                20                  25                  30

Arg Gly Leu Phe Arg Leu Thr Gly Asp His Asp Pro Asn Pro Glu Glu
            35                  40                  45

Arg Pro Pro Pro Leu Glu Gly Glu Val Glu Gly His Pro Pro Pro Pro
        50                  55                  60

Val Thr Asn Pro Pro Gly His
 65                  70

<210> SEQ ID NO 132
<211> LENGTH: 95
<212> TYPE: PRT
<213> ORGANISM: Human papillomavirus type 25

<400> SEQUENCE: 132

Pro Pro Ala Gly His Asp Asp Ser Lys Pro Lys Arg Ala Arg Gly Asp
 1               5                  10                  15

Gln Gly Pro Ser Pro Gly Pro Gly Pro Ser Pro Ala Pro Val Ser Asp
                20                  25                  30

Arg Gly Arg Gly Arg Gly Arg Gly Leu Asn Leu Ser Arg Leu Ser Gly
            35                  40                  45

Asp Gln Asp Pro Asp Pro Glu Glu Lys Pro Gln Pro Glu Gly Glu Val
        50                  55                  60

Gln Gly His Pro Gln Pro Pro Val Thr Glu Pro Gln Gly His Leu
 65                  70                  75                  80

Pro Pro Pro Pro Leu Pro Pro Pro Asn Gly His Asn Asp Arg Asp
                85                  90                  95

<210> SEQ ID NO 133
<211> LENGTH: 99
<212> TYPE: PRT
<213> ORGANISM: Human papillomavirus type 20

<400> SEQUENCE: 133

Gly Thr Asp Gly Asp Leu Pro Val Gly Gln Gly Glu Gln Pro Lys Arg
 1               5                  10                  15

Ala Arg Gly Asp Gly Pro Gly Gln Ser Pro Ser Pro Ser Pro Gly Arg
                20                  25                  30

Gly Arg Gly Arg Gly Thr Gly Leu Gly Leu Gly Leu Gly Leu Asn Arg
            35                  40                  45

Arg Ala Gly Gly Leu Gly Thr Asp His Asp Pro Asp Pro Glu Gly Glu
        50                  55                  60

Ser Pro Ser Ala Pro Leu Pro Pro Pro Gln Pro Pro Pro Asp Gly
 65                  70                  75                  80

Gln Val Glu Gly His Pro Pro Pro Pro Pro Pro His Asn Gly
                85                  90                  95

Arg Asp Ser

<210> SEQ ID NO 134
<211> LENGTH: 106
<212> TYPE: PRT
<213> ORGANISM: Human papillomavirus type 21

<400> SEQUENCE: 134

Gly Thr Asp Gly Asp Arg Pro Val Gly Pro Gly Glu Arg Pro Lys Arg
1               5                   10                  15

Ile Lys Gly Gly Asp Arg Gly Pro Ser Pro Gly Arg Gly Arg Gly Arg
            20                  25                  30

Gly Arg Gly Ser Asp Pro Asp Pro Gly Pro Asp Pro Gly Pro Ile Pro
        35                  40                  45

Gly Pro Gly Leu Asn Arg Leu Thr Ser Arg Asn Thr Asp Ser Asp Pro
    50                  55                  60

Glu Gly Lys Cys Pro Ser Ser Leu Pro Pro Pro Pro Pro Pro Pro Pro
65                  70                  75                  80

Gln Pro Thr Thr Pro Pro Glu Gly Gln Gly Glu Gly His Pro Pro Pro
                85                  90                  95

Pro Pro Pro Pro Pro Asn Gly His Asp Gly
            100                 105

<210> SEQ ID NO 135
<211> LENGTH: 88
<212> TYPE: PRT
<213> ORGANISM: Human papillomavirus type 14

<400> SEQUENCE: 135

Glu Gly Thr Asp Ala Asp Arg Pro Val Gly Pro Gly Glu Arg Pro Lys
1               5                   10                  15

Arg Gly Arg Gly Gly Asp Arg Gly Pro Ser Pro Gly Arg Gly Arg Gly
            20                  25                  30

Arg Gly Leu Gly Ser Asp Leu Asp Pro Gly Arg Asn Arg Leu Ser Gly
        35                  40                  45

Gly Leu Gly Thr Asp Gln Asp Pro Asp Pro Lys Lys Lys Cys Pro
    50                  55                  60

Glu Ser Gln Pro Pro Glu Gly Glu Val Glu Gly His Pro Pro Pro
65                  70                  75                  80

Pro Pro Asn Gly His Asn Gly His
                85

<210> SEQ ID NO 136
<211> LENGTH: 90
<212> TYPE: PRT
<213> ORGANISM: Human papillomavirus type 5

<400> SEQUENCE: 136

Ser Gln Gly Asp Arg Lys Arg Ser Lys Gly Asp Gln Gly Pro Asp Thr
1               5                   10                  15

Gly Pro Gly Leu Gly Pro Gly Arg Gly Pro Ser Pro Lys Pro Thr Pro
            20                  25                  30

Leu Gly Pro Pro Gly Pro Gly Pro Arg Arg Ser Pro Arg Leu Gly
        35                  40                  45

Pro Leu Gln Ala Asp Arg Asp Pro Glu Glu Gly Pro Gln Pro Ala
    50                  55                  60

Glu Gly Glu Val Glu Gly His Pro Gly Gly Asp Gln Gly His Pro Pro
65                  70                  75                  80

Pro Pro Pro Pro Ala Pro His Asn Gly His
                85                  90

```
<210> SEQ ID NO 137
<211> LENGTH: 87
<212> TYPE: PRT
<213> ORGANISM: Human papillomavirus type 36

<400> SEQUENCE: 137

Gly Gln Gly Asp Arg Lys Arg Ser Lys Gly Asp Gln Gly Pro Asp Thr
 1               5                  10                  15

Asp Pro Leu Gly Pro Asp Arg Gly Pro Ser Pro Gly Pro Thr Pro Gln
            20                  25                  30

Pro Leu Gly Leu Pro Pro Gly Leu Gly Pro Arg Arg Ser Pro Arg
        35                  40                  45

Leu Gly Ser Ser Gly Tyr Gln Pro Asp His Asp Pro Glu Ala Pro Leu
    50                  55                  60

Glu Gly Glu Val Glu Gly Gly His Gly His His Pro Pro Pro Pro
65                  70                  75                  80

Pro Pro Pro Pro Pro Thr Asn
                85

<210> SEQ ID NO 138
<211> LENGTH: 87
<212> TYPE: PRT
<213> ORGANISM: Human papillomavirus type 47

<400> SEQUENCE: 138

Gln Gly Asp Arg Lys Arg Thr Lys Gly Asp Pro Asp Pro Asp Pro Gly
 1               5                  10                  15

Arg Gly Pro Val Leu Lys Pro Thr Leu Pro Pro Pro Pro Pro Pro Pro
            20                  25                  30

Pro Thr Gly Pro Gly Leu Arg Arg Ser Thr Arg Leu Val Leu Val Pro
        35                  40                  45

Gly Gln Gly Pro Pro Pro Asp Leu Pro Ala Pro Val Glu Gly Glu
    50                  55                  60

Val Glu Gly His Pro Gln Gly Lys Asp Arg Asp His Pro Pro Pro Thr
65                  70                  75                  80

Pro Gln Asn Gly His Gly Lys
                85

<210> SEQ ID NO 139
<211> LENGTH: 76
<212> TYPE: PRT
<213> ORGANISM: Human papillomavirus type 12

<400> SEQUENCE: 139

Gly Asp Arg Lys Arg Ser Lys Gly Asp Gln Gly Arg Asp Thr Ala Pro
 1               5                  10                  15

Ser Leu Thr Pro Gly Arg Ala Pro Ser Pro Lys Pro Gly Pro Leu Ala
            20                  25                  30

Pro Pro Pro Tyr Pro Gly Pro Pro Gly Pro Arg Arg Ser His Arg Leu
        35                  40                  45

Gly Thr Gly Gly Arg Asp Arg Asn Pro Glu Glu Gly Val Glu Gly
    50                  55                  60

His Pro Pro Thr Pro Pro Leu Ser Gly Gly Asp Pro
65                  70                  75

<210> SEQ ID NO 140
<211> LENGTH: 91
```

<212> TYPE: PRT
<213> ORGANISM: Human papillomavirus type 8

<400> SEQUENCE: 140

Gln Asp Arg Lys Lys Ser Arg Gly Asp Gln Gly Arg Asp Thr Ala Pro
 1               5                  10                  15

Gly Leu Ala Pro Gly Arg Ser Pro Gly Leu Gly Pro Leu Ala Pro Pro
             20                  25                  30

Pro Tyr Pro Gly Pro Gly Pro Arg Arg Ser Pro Arg Gln Phe Gly Pro
         35                  40                  45

Gly Pro Asp Arg Asp Pro Glu Asp Gly Leu Gln Pro Pro Leu Gly Glu
     50                  55                  60

Gly Gln Val Glu Gly His Pro Gly Asp Gly Asp Gln Pro Gln Gly His
 65                  70                  75                  80

Pro Pro Pro Thr Pro Ser Asn Gly His Lys Gly
                 85                  90

<210> SEQ ID NO 141
<211> LENGTH: 70
<212> TYPE: PRT
<213> ORGANISM: Human papillomavirus type 24

<400> SEQUENCE: 141

Pro Leu Thr Pro Asp Ala Asp Asp Pro Arg Pro Gly Lys Arg Ser
 1               5                  10                  15

Lys Gly Asp Glu His Gly Pro Ala Pro Gly Arg Ala Ala Ala Pro Leu
             20                  25                  30

Lys Leu Asp Leu Asp Pro Pro Gln Gly Gly Pro Asp Gln Pro Pro Gly
         35                  40                  45

Ala Thr Gly Gly Val Gly Glu Thr Pro Pro Glu Gly Asn Glu Glu Ser
     50                  55                  60

Gln Pro Pro Pro Gly Glu
 65                  70

<210> SEQ ID NO 142
<211> LENGTH: 61
<212> TYPE: PRT
<213> ORGANISM: Human papillomavirus type 15

<400> SEQUENCE: 142

Thr Thr Glu Lys Asn Leu Ala Gln Pro Pro Pro Gly Gly Arg Lys
 1               5                  10                  15

Asp Lys Asp Lys Asp Lys Lys Thr Gln Gln Gly Asp Gln Gly Pro Pro
             20                  25                  30

Gln Gly Gly Asp Lys Lys Ser Pro Gly Glu Gly Thr Ser Ala Asp Gly
         35                  40                  45

Asp Asp Pro Glu Lys Pro Pro Ser Pro Pro Gly Glu
     50                  55                  60

<210> SEQ ID NO 143
<211> LENGTH: 60
<212> TYPE: PRT
<213> ORGANISM: Human papillomavirus type 17

<400> SEQUENCE: 143

Asp Thr Gly Gly Lys Arg Leu Ala Leu Gln Pro Pro Pro Gly Thr
 1               5                  10                  15

Lys Asp Lys Thr Ser Asp Asp Gln Gly Pro Pro His Gly Gly Asp Lys
             20                  25                  30

Gln Ser Pro Gly Glu Gly Ser Asp Ala Ser Gly Asp Glu Asn Ala Pro
        35                  40                  45

Thr Pro Glu Thr Pro Gln Asp Pro Pro Thr Gly Glu
    50                  55                  60

<210> SEQ ID NO 144
<211> LENGTH: 62
<212> TYPE: PRT
<213> ORGANISM: Human papillomavirus type 37

<400> SEQUENCE: 144

Glu Glu Lys His Leu Ala Leu Gln Pro Pro Pro Gly Lys Lys Asp
1               5                  10                  15

Lys Glu Lys Thr Pro Gln Gln Gly Asp Gln Gly Pro Pro Gly Gly
                20                  25                  30

Asn Lys Gln Pro Pro Gly Glu Gly Thr Asp Ala Asp Gly Asp Glu Asn
        35                  40                  45

Ala Pro Thr Pro Glu Thr Pro Pro Val Pro Pro Thr Gly Glu
    50                  55                  60

<210> SEQ ID NO 145
<211> LENGTH: 61
<212> TYPE: PRT
<213> ORGANISM: Human papillomavirus type 9

<400> SEQUENCE: 145

Pro Pro Pro Gly Arg Lys Asp Arg Asp Lys Glu Lys Glu Lys Glu Lys
1               5                  10                  15

Glu Lys Glu Lys Lys Pro Thr Thr Gly Asp Lys Gly Pro Asp Pro Arg
                20                  25                  30

Val Glu Gln Lys Pro Lys Gly Glu Gly Ser Asp Gly Asp Glu Glu Gly
        35                  40                  45

Pro Pro Pro Gln Thr Pro Leu Pro Pro Thr Gly Glu
    50                  55                  60

<210> SEQ ID NO 146
<211> LENGTH: 57
<212> TYPE: PRT
<213> ORGANISM: Human papillomavirus type 22

<400> SEQUENCE: 146

Leu Val Leu Gln Ser Pro Pro Ser Gly Gly Lys Lys Gly Glu Arg Asp
1               5                  10                  15

Lys Asp Lys Lys Pro Gln Gln Gly Glu Glu Lys Pro Asp Gln Gly Pro
                20                  25                  30

Glu Ala Pro Ser Ser Gly Glu Gly Gly Pro Pro Asp Asp Pro Ser Pro
        35                  40                  45

Glu Asn Pro Gln Asn Pro Pro Gly Gly
    50                  55

<210> SEQ ID NO 147
<211> LENGTH: 55
<212> TYPE: PRT
<213> ORGANISM: Human papillomavirus type 23

<400> SEQUENCE: 147

Lys His Leu Ala Leu Gln Pro Pro Gly Gly Lys Lys Asp Lys Glu
1               5                  10                  15

Lys Lys Pro Ser Pro Gly Glu Glu Lys Pro Asp Gln Gly Pro Gly Ala

-continued

```
                 20                  25                  30

Glu Ser Asn Gly Gly Gly Lys Pro Lys Asp Pro Pro Glu Glu
         35                  40                  45

Pro Gln Asn Pro Pro Gly Gly
         50                  55

<210> SEQ ID NO 148
<211> LENGTH: 63
<212> TYPE: PRT
<213> ORGANISM: Human papillomavirus type 38

<400> SEQUENCE: 148

Asp Thr Gly Glu Lys His Leu Ala Leu Gln Pro Pro Ala Gly Lys
  1               5                  10                  15

Gly Lys Asp Lys Glu Lys Pro Gln Ala Pro Lys Gly Glu Glu Lys Ala
                 20                  25                  30

Asp Gln Gly Pro Glu Ala Pro Thr Gly Glu Gly Gly Thr Pro Gly Asp
         35                  40                  45

Pro Pro Pro Glu Asp Pro Gln Ser Pro Pro Pro Gly Glu Gly Glu
         50                  55                  60

<210> SEQ ID NO 149
<211> LENGTH: 75
<212> TYPE: PRT
<213> ORGANISM: Human papillomavirus type 49

<400> SEQUENCE: 149

Thr Leu Val Leu Gln Gln Pro Pro Thr Pro Gly Lys Arg Ser Arg Asp
  1               5                  10                  15

Asp Asp Pro Gly Leu Glu Pro Gly Pro Ala Asp Gly Lys Arg Ala Pro
                 20                  25                  30

Gln Gly Pro Lys Lys Pro Ala Val Pro Asp Pro Asp Pro Asp Pro Leu
         35                  40                  45

Pro Glu Asp Pro Glu Gly Pro Glu Asp Leu Ser Gln Pro Pro Glu Ile
         50                  55                  60

Pro Ala Pro Arg Glu Pro Ala Gly Ala Glu Gly
         65                  70                  75

<210> SEQ ID NO 150
<211> LENGTH: 52
<212> TYPE: PRT
<213> ORGANISM: Human papillomavirus type 4

<400> SEQUENCE: 150

Pro Ser Arg Arg Ala Leu Leu Glu Gly Gly Asn Arg Gly Asn Pro Thr
  1               5                  10                  15

Arg Pro Pro Pro Arg Pro Leu Lys Pro Arg Glu Tyr Asp Tyr Asp Glu
                 20                  25                  30

Asp Asp Glu Lys Glu Asn Gln Gly Pro Gly Gln Glu Lys Pro Pro Ala
         35                  40                  45

Lys Glu Glu Glu
         50

<210> SEQ ID NO 151
<211> LENGTH: 54
<212> TYPE: PRT
<213> ORGANISM: Human papillomavirus type 65

<400> SEQUENCE: 151
```

Pro Ser Leu Pro Arg Arg Ala Leu Val Val Gly Gly Asn Arg Gly Asn
1               5                   10                  15

Leu Asn Arg Pro Pro Gln Arg Pro Lys Pro Arg Gly Tyr Glu Tyr
            20                  25                  30

Asp Glu Asp Asp Asp Lys Glu Asn Gln Gly Pro Gly Gln Glu Arg Pro
        35                  40                  45

Pro Ala Lys Glu Glu Glu
        50

<210> SEQ ID NO 152
<211> LENGTH: 44
<212> TYPE: PRT
<213> ORGANISM: Human papillomavirus type 48

<400> SEQUENCE: 152

Leu Glu Gly Asp Arg Ala Ser Gln Lys Thr Pro Thr Pro Ser Arg Pro
1               5                   10                  15

Pro Pro Arg His Pro Asp Tyr Glu Ser Asp Asp Asp Glu Asn Arg Glu
            20                  25                  30

Asn Leu Glu Pro Pro Thr Pro Pro His Pro Glu Asp
        35                  40

SEQ ID NO 153
LENGTH: 48
<212> TYPE: PRT
<213> ORGANISM: Human papillomavirus type 50

<400> SEQUENCE: 153

Ala Asn Arg Lys Asp Leu Glu Ala Val Asn Gln Lys Pro Tyr Arg Thr
1               5                   10                  15

Pro Asn His Pro Pro Arg His Gln Gln Tyr Asp Phe Asp Glu Asp Asp
            20                  25                  30

Glu Lys Glu Asn Thr Ile Pro Thr Asp Thr Glu Ser His Asn Gln Asn
        35                  40                  45

<210> SEQ ID NO 154
<211> LENGTH: 47
<212> TYPE: PRT
<213> ORGANISM: Human papillomavirus type 60

<400> SEQUENCE: 154

Leu Pro Thr Glu Asp Arg Pro His Lys Arg Glu Ser Leu Ala Leu Pro
1               5                   10                  15

Arg Arg Arg Val Leu Phe Asp Tyr Asp Ala Glu Asp Pro Thr Ser Asn
            20                  25                  30

Lys Glu Asn Tyr Pro Pro Glu Ser Arg Pro Val Pro Lys Asp Ala
        35                  40                  45

<210> SEQ ID NO 155
<211> LENGTH: 39
<212> TYPE: PRT
<213> ORGANISM: Bovine papillomavirus type 1

<400> SEQUENCE: 155

Pro Ser Leu Ser Leu Leu Cys Ser Ala Pro Pro Ala Val Pro Ser
1               5                   10                  15

Glu Gln Ala Ser Val Gly Tyr Glu Thr Val Leu Ala Arg Thr Pro Thr
            20                  25                  30

Ile Phe Leu Gln Ala Arg Gly
        35

<210> SEQ ID NO 156
<211> LENGTH: 39
<212> TYPE: PRT
<213> ORGANISM: Unknown
<220> FEATURE:
<223> OTHER INFORMATION: Description of Unknown Organism: Non-Human
      Virus

<400> SEQUENCE: 156

Pro Ser Leu Ser Leu Leu Cys Ser Ala Pro Pro Ala Tyr Pro Ser
 1               5                  10                  15

Glu Gln Ala Ser Val Gly Tyr Glu Thr Val Leu Ala Arg Thr Pro Thr
                20                  25                  30

Ile Phe Leu Gln Ala Arg Gly
            35

<210> SEQ ID NO 157
<211> LENGTH: 43
<212> TYPE: PRT
<213> ORGANISM: European elk papillomavirus

<400> SEQUENCE: 157

Pro Thr Gln Pro Thr Glu Pro Cys Leu Thr Leu Leu Leu Asp Asn Pro
 1               5                  10                  15

Pro Phe Val Ala Pro Ser Glu Leu Ala Lys Thr Gly Val Gly Pro Phe
                20                  25                  30

Thr Ala Arg Leu Pro Thr Ala His His His Pro
            35                  40

<210> SEQ ID NO 158
<211> LENGTH: 34
<212> TYPE: PRT
<213> ORGANISM: deer papillomavirus

<400> SEQUENCE: 158

Thr Leu Leu Leu Glu Ala Thr Pro Phe Thr Val Pro Ser Glu Leu Ala
 1               5                  10                  15

Lys Thr Gly Val Gly Pro Leu Thr Ala Arg Leu Pro Thr Ala His His
                20                  25                  30

Ser Pro

<210> SEQ ID NO 159
<211> LENGTH: 50
<212> TYPE: PRT
<213> ORGANISM: Bovine papillomavirus type 4

<400> SEQUENCE: 159

Pro Asp Leu Pro Glu Thr Pro Gly Ala Gly Ser Arg Gly Arg Ser Arg
 1               5                  10                  15

Leu Arg Asp Arg Asp His Gly His Asp His Asp Arg Leu Arg Arg Gly
                20                  25                  30

Arg Thr Pro Val Asp Glu Thr Arg Gly Tyr Arg Val Pro Gly Asp Pro
            35                  40                  45

Arg Glu
     50

<210> SEQ ID NO 160
<211> LENGTH: 50
<212> TYPE: PRT
<213> ORGANISM: Human papillomavirus type 41

<400> SEQUENCE: 160

Pro Gln Arg Tyr Tyr Asp Arg Arg Gly Arg Asp Asp Ala Glu Thr Arg
1               5                   10                  15

Lys Arg Gly Ser Arg Ser Pro Gln Pro Leu Ser Glu Asp Glu Glu Leu
            20                  25                  30

Thr Asp Ala Asp Pro Pro Arg Arg Pro Asn Ala Gly Pro Arg Arg Arg
        35                  40                  45

Leu Phe
    50

<210> SEQ ID NO 161
<211> LENGTH: 47
<212> TYPE: PRT
<213> ORGANISM: Canine oral papillomavirus

<400> SEQUENCE: 161

Leu Pro Pro Gly Lys Gly Arg His Gly Gly Leu Asp Gly Gly Arg Arg
1               5                   10                  15

Gly Ser Pro Glu Gly Gln Glu Asp Glu Glu Asp Ser Asp Glu Glu Glu
            20                  25                  30

Ala Glu Asn Tyr Pro Pro Ser Arg Ser Arg Pro Arg Arg Gly Arg
        35                  40                  45

<210> SEQ ID NO 162
<211> LENGTH: 34
<212> TYPE: PRT
<213> ORGANISM: Unknown Organism
<220> FEATURE:
<223> OTHER INFORMATION: Description of Unknown Organism: cottontail
      rabbit papillomavirus

<400> SEQUENCE: 162

Gln Gly Pro Lys Pro Arg Val His Trp Ala Asp Glu Gly Gln Gly His
1               5                   10                  15

Gln Gly Cys Asn Glu Gly Arg Gln Ser Asn Glu Asn Arg Pro Pro Arg
            20                  25                  30

Thr Lys

<210> SEQ ID NO 163
<211> LENGTH: 61
<212> TYPE: PRT
<213> ORGANISM: Unknown Organism
<220> FEATURE:
<223> OTHER INFORMATION: Description of Unknown Organism: Rabbit Oral
      Papillomavirus

<400> SEQUENCE: 163

Leu Gln Tyr Pro Gln Ala Pro Arg Thr Ile Arg Lys Pro Arg Ser Ser
1               5                   10                  15

Arg Tyr Arg Gly Arg Phe Leu Val Thr Asp Gly Gly Asp Pro Asp Pro
            20                  25                  30

Gln Glu Leu Asp Ser Thr Gln Gln Asp Pro Glu Asp Lys Glu Asn Ile
        35                  40                  45

Pro Pro Thr Ser Thr Pro Thr Pro Ser Pro Pro Thr Pro
    50                  55                  60

<210> SEQ ID NO 164
<211> LENGTH: 48
<212> TYPE: PRT
<213> ORGANISM: Human papillomavirus type 1a

<400> SEQUENCE: 164

Thr Pro Pro Ser Asn Arg Arg Pro Ser Thr Thr Pro Asn Ser Gln Asp
1               5                   10                  15
Arg Gly Arg Pro Arg Arg Ser Asp Lys Asp Ser Arg Lys His Leu Tyr
            20                  25                  30
Ala Asp Gly Leu Thr Asp Gly Glu Asp Pro Glu Val Pro Glu Val Glu
        35                  40                  45

<210> SEQ ID NO 165
<211> LENGTH: 40
<212> TYPE: PRT
<213> ORGANISM: Human papillomavirus type 63

<400> SEQUENCE: 165

Lys Leu Pro Glu Lys Gln Arg Arg Gly Arg Asp Thr Thr Arg Asn
1               5                   10                  15
Arg Arg Leu Phe Ala Ser Asp Gly Pro Thr Asp Glu Glu Gly Pro Glu
            20                  25                  30
Val Pro Glu Ile Pro Pro Ser Asp
        35                  40

<210> SEQ ID NO 166
<211> LENGTH: 48
<212> TYPE: PRT
<213> ORGANISM: Mastomys natalensis

<400> SEQUENCE: 166

Ile Pro Arg Val Ser Leu Gln Asp Lys Thr Thr Gly Gly Asn Gln Gln
1               5                   10                  15
Arg Arg Arg Arg Arg Gly Glu Arg Gly Ala Arg Thr Pro Ser Pro Glu
            20                  25                  30
Thr Thr Ala Gln Arg Pro Lys Arg Pro Arg Arg Ala Cys Thr Arg Lys
        35                  40                  45

<210> SEQ ID NO 167
<211> LENGTH: 15
<212> TYPE: PRT
<213> ORGANISM: Human papillomavirus type 16

<400> SEQUENCE: 167

Arg Pro Ile Pro Lys Pro Ser Pro Trp Ala Pro Lys Lys His Arg
1               5                   10                  15

<210> SEQ ID NO 168
<211> LENGTH: 12
<212> TYPE: PRT
<213> ORGANISM: Human papillomavirus type 16

<400> SEQUENCE: 168

Pro Lys Pro Ser Pro Trp Ala Pro Lys Lys His Arg
1               5                   10

<210> SEQ ID NO 169
<211> LENGTH: 13
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 169

-continued

Met Ala Asp Pro Ala Ala Ala Thr Lys Tyr Pro Leu Cys
1               5                  10

<210> SEQ ID NO 170
<211> LENGTH: 8
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 170

Leu Leu Arg Gly Ala Phe Asp Tyr
1               5

<210> SEQ ID NO 171
<211> LENGTH: 11
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 171

Asn Ser Arg Asp Ser Ser Gly Gly Asn Ala Val
1               5                   10

<210> SEQ ID NO 172
<211> LENGTH: 8
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 172

Leu Val Gln Gly Ser Phe Asp Tyr
1               5

<210> SEQ ID NO 173
<211> LENGTH: 8
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 173

Gln Ala Asp Ser Ser Thr His Val
1               5

<210> SEQ ID NO 174
<211> LENGTH: 72
<212> TYPE: DNA
<213> ORGANISM: Artificial Sequence
<220> FEATURE:
<223> OTHER INFORMATION: Description of Artificial Sequence:  synthetic
      oligonucleotide
<220> FEATURE:
<221> NAME/KEY: Misc_Feature
<222> LOCATION: (24)...(49)
<223> OTHER INFORMATION: "n" at positions 24-49 can be any of G, A, T,
      or C

<400> SEQUENCE: 174
cctgttgtga gcctcctgtc gaannnnnnn nnnnnnnnnn nnnnnnnnnt tgagcgttta     60
ttcttgtctc cc                                                        72

<210> SEQ ID NO 175
<211> LENGTH: 40
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 175
taatacgact cactataggg agacaagaat aaacgctcaa                          40

<210> SEQ ID NO 176
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 176
gcctgttgtg agcctcctgt cgaa                                          24

<210> SEQ ID NO 177
<211> LENGTH: 90
<212> TYPE: DNA
<213> ORGANISM: Artificial Sequence
<220> FEATURE:
<223> OTHER INFORMATION: Description of Artificial Sequence: synthetic
      oligonucleotide, n = any randon nucleotide.
<220> FEATURE:
<221> NAME/KEY: Misc_Feature
<222> LOCATION: (41)...(66)
<223> OTHER INFORMATION: "n" at positions 41-66 can be any of G, A, T,
      or C

<400> SEQUENCE: 177
taatacgact cactataggg agacaagaat aaacgctcaa nnnnnnnnnn nnnnnnnnnn    60
nnnnnnttcg acaggaggct cacaacaggc                                    90

<210> SEQ ID NO 178
<211> LENGTH: 73
<212> TYPE: RNA
<213> ORGANISM: Artificial Sequence
<220> FEATURE:
<223> OTHER INFORMATION: Description of Artificial Sequence:in vitro
      transcription product from SEQ ID NO: 177, n = any random
      nucleotide.
<220> FEATURE:
<221> NAME/KEY: Misc_Feature
<222> LOCATION: (24)...(49)
<223> OTHER INFORMATION: "n" at posistion 24-49 can be any of G, A, U,
      or C

<400> SEQUENCE: 178
gggagacaag aauaaacgcu caannnnnnn nnnnnnnnnn nnnnnnnnnu ucgacaggag    60
gcucacaaca ggc                                                      73

<210> SEQ ID NO 179
<211> LENGTH: 4
<212> TYPE: PRT
<213> ORGANISM: Artificial Sequence
<220> FEATURE:

```
-continued

<223> OTHER INFORMATION: Description of Artificial Sequence: synthetic
      peptide

<400> SEQUENCE: 179

Asp Glu Ala Asp
 1
```

SCREENING FOR PAPILLOMA VIRUSES

This application is a continuation of Ser. No. 09/314,268, filed May 18, 1999, now U.S. Pat. No. 6,346,377 issued Feb. 12, 2002, which is a continuation of international application No. PCT/GB97/03321, which designated the United States and was filed Dec. 3, 1997, published in English and which claims priority to foreign application GB9718745.4, filed Sep. 5, 1997, and GB9625142.6, filed Dec. 3, 1996.

FIELD OF THE INVENTION

This invention relates to a method of screening for precursor lesions which can lead to cervical malignancy, methods of detecting and typing HPV infections, and reagents of use in the above methods.

BACKGROUND OF THE INVENTION

Papillomaviruses (PVs) cause epithelial rumours in humans which vary in severity depending on the site of infection and the HPV (human papilloma virus) type involved (Laimins-, 1993; Villiers de, 1994). Low risk types such as HPV 1 or HPV63 (Egawa et al. 1993a: Egawa et al. 1993b) cause benign cutaneous warts which progress to malignancy only rarely, while high risk viruses such as HPV 16 and HPV31 cause flat warts at mnucosal sites, and are associated with high grade cervical intraepithelial neoplasia (CIN) and cancer (Schneider, 1994). Formation of an HPV-induced tumour is thought to require infection of an epithelial basal cell, and the expression of viral early proteins in order to stimulate cell proliferation. The late stages of the virus life cycle, which ultimately lead to the production of infectious virions, are initiated only as the infected cell migrates through the upper differentiated layers of the epidermis. Viral and cellular events which influence HPV late gene expression have not been characterised as. until recently, there has been no convenient system for mimickina productive infection in vitro (Laimins, 1993)

Studies on naturally-occurring warts have revealed the virus to encode three late proteins—L1 and L2, which are virion coat proteins (Doorbar et al, 1987), and E1^E4, a non-structural late protein of unknown function (Doorbar et al, 1986). In HPV1-induced warts the E1^E4 protein is first expressed in cells of the lower spinous layer, and assembles into distinctive cytoplasmic and nuclear inclusions. During terminal differentiation it is post-transcriptionally modified by phosphorylation (Grand et al, 1989) and by removal of sequences from the N-terminus (Doorbar et al, 1988; Roberts et al, 1994). The E1^E4 proteins of high risk viruses have been poorly characterised, because it has been thought that HPV16-induced lesions contain only small numbers of productively infected cells, and that these contain only low levels of E4 (Doorbar et al, 1996b: Crum et al, 1990). A single Mab (TVG 402) to HPV16 E1^E4 has been used to locate the protein to the cytoplasm but was reported not to work well on paraffin-embedded archival material (Doorbar et al, 1992). Furthermore, polyclonal antibody studies on the E4 proteins of mucosal viruses have yielded conflicting results. One study has supported the above findings (Crum et al, 1990), while another has indicated that the protein is located to the nucleus (Palefsky et al. 1991).

In many countries there are screenig prograrmes to detect the presence of cervical carcinoma at an early stage. Generally such prdgrammes operate by obtaining cervical smears from women potentially at risk of developing cervical cancer, with the resulting smears routinelv beinz examined bv conventional histopathological techniques. These techniques are laborious and time-consuming, require considerable experience to interpret results correctly, and frequently give rise to relatively large percentages of false positive results, causing unnecessary alarm. False negatives can occur when screening is carried out by inexperienced personnel and can lead to the classification of pre-cancerous lesions as normal. There is thus a need for an improved cervical cancer screening method.

It is well known that there is a very strong correlation between HPV-infection and development of cervical carcinoma: over 90% of women with cervical carcinoma show evidence of HPV infections of the cervix. Accordingly, one possible alternative to conventional histopathological examination of cervical smears is to examine samples for evidence of HPV infection. For example, there have been numerous proposals to screen for cervical carcinoma by performing DNA hybridisation assays on samples, using nucleic acid probes specific for HPV sequences. Such hybridisation assays are generally favoured by those skilled in the art, because of the ready availability of suitable reagents and because of their high specificity.

Thus, for example in Fields Virology (Fields et al, [Eds.] *Virology* Vol. 2, p 2099, 3rd Edn. (1996) Raven Press, New York), an authoritative virology text book, it is stated that "Diagnosis of an HPV type in a tissue requires nucleic acid hybridization studies".

In contrast, screening for cervical carcinoma by detection of expression of HPV polypeptides has generally been disregarded, being considered unsuitable for a number of reasons, primarily because of the difficulty in obtaining suitable reagents and, more significantly, many HPVs produce very little virus protein in mucosal infections, making detection difficult, uncertain and unreliable. Thus, in Fields Virology (cited above) it is state that "immunologic detection of viral capsid antigens" is "of limited value". The possibility of immunologic detection of other viral antigens is not even considered. If one were to develop a screening method based on detection of expression of viral proteins, the most likely choice of target would be those proteins which are best-characterised, such as L1 or L2. The function of E4 protein is at present unknown. Its expression pattern in cervical lesions has not been determined conclusively in the prior art so the molecule has not been an obvious choice for selection as a target for detecting HPV infection.

SUMMARY OF THE INVENTION

In accordance with the present invention, it has now been demonstrated that HPV infection can be detected in a sample taken from a patient by using molecules which bind specifically to E4 protein of HPVs. In particular, the invention provides a method of screening samples for pre-cancerous cervical lesions, using molecules which bind specifically to HPV E4 protein.

The present studies have clearly demonstrated HPV16 E4 protein to be cytoplasrnic, and to be produced in cells supporting vegetative viral DNA replication.

In a first aspect the invention provides a method of detecting a papilloma virus infection in an organism, the method comprising the steps of: obtaining a sample of the organism's cells from the site of potential papilloma virus infection; contacting the cells with a molecule that binds specifically to papilloma virus E4 protein; and monitoring said binding.

In particular, the invention provides a method of screening for pre-cancerous cervical lesions, comprising the steps of: obtaining a sample of cervical cells from a subject; contacting the cells with a molecule that binds specifically to HPV E4 protein; and monitoring said binding.

Moreover, the invention provides a method of determining the type(s) of HPV infection in a patient, the method comprising the steps of: obtaining a sample of the patient's cells from the site of HPV infection; contacting the cells with a molecule that binds specifically to a subset of HPV E4 proteins; and monitoring said binding.

In a further aspect the invention provides an antibody molecule or an antigen-binding variant thereof, which binds specifically to HPV E4 protein in the region of amino acid residues RPIPKPSPWAPKKHRRLSDQDSQTP (SEQ ID NO: 4) of HPV16 E4 protein, or the corresponding hydrophilic acid/base-rich region of other HPV E4 proteins.

The invention moreover concerns the use of molecules capable of binding to E4 to target antiviral agents capable of destroying papilloma viruses and/or cells infected by papilloma viruses. Such molecules may be antibodies or peptides as described above and exemplified herein, optionally conjugated to anticancer or antiviral agents.

BRIEF DESCRIPTION OF THE DRAWINGS

FIG. 9 is an amino acid sequence alignment of part of HPV E4 proteins.

Figure 1:
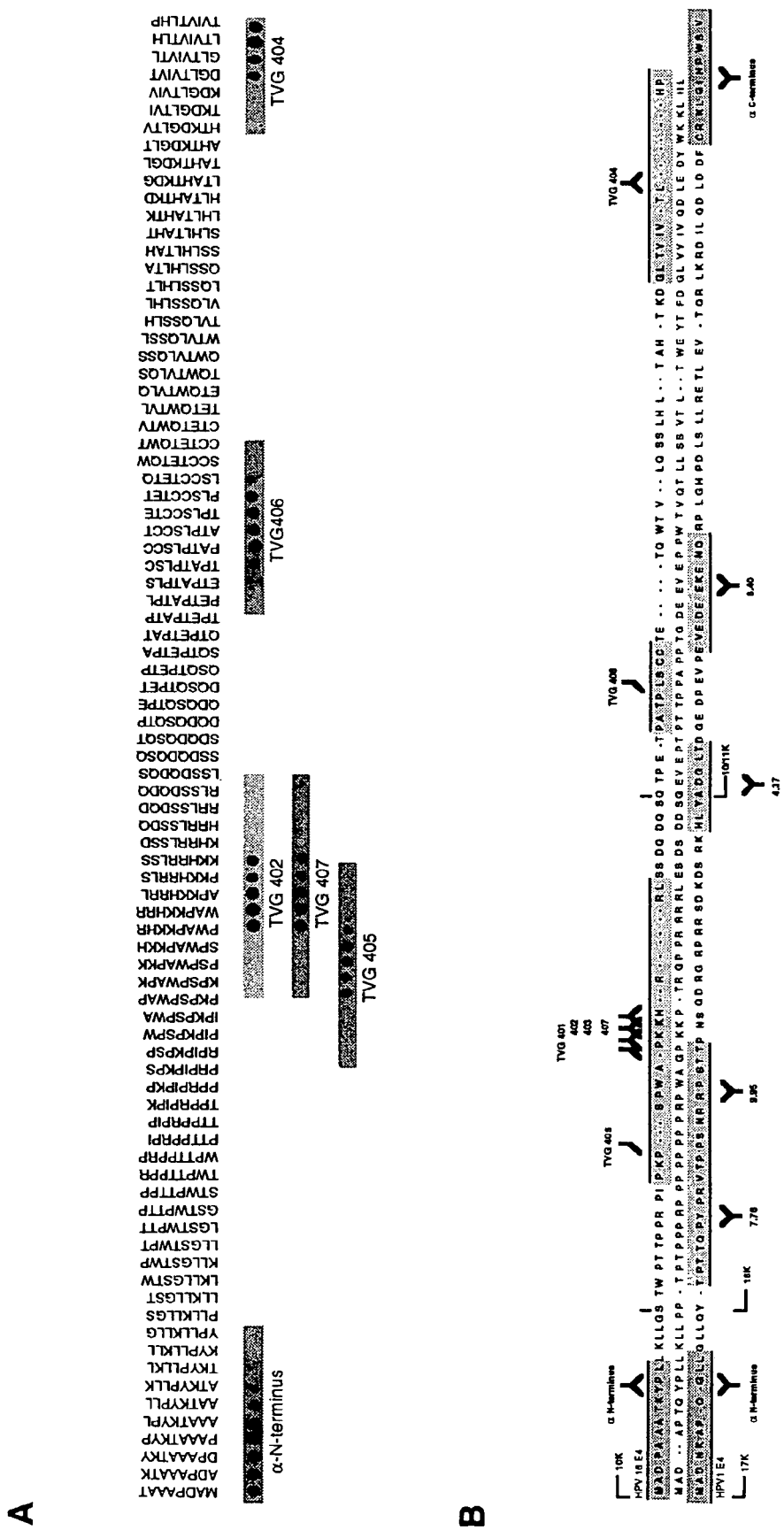
FIG. 1A shows the amino acid sequence of HPV16 E4 protein and the binding sites of various antibody molecules or E4-specific antigen-binding fragments of antibodies; octapeptide sequences are identified as follows: MADPAAAT, SEQ ID NO:5; ADPAAATK, SEQ ID NO:6; DPAAATKY, SEQ ID NO:7; PAAATKYP, SEQ ID NO:8; AAATKYPL, SEQ ID NO:9; AATKYPLL, SEQ ID NO:10; ATKYPLLK, SEQ ID NO:11; TKYPLLKL, SEQ ID NO:12; KYPLLKLL, SEQ ID NO:13; YPLLKLLG, SEQ ID NO:14; PLLKLLGS. SEQ ID NO:15; LLKLLGST, SEQ ID NO:16; LKLLGSTW, SEQ ID NO:17; KLLGSTWP, SEQ ID NO:18; LLGSTWPT, SEQ ID NO:19; LGSTWPTT, SEQ ID NO:20; GSTWPTTP, SEQ ID NO:21; STWPTTPP, SEQ ID NO:22; TWPTTPPR, SEQ ID NO:23; WPTTPPRP, SEQ ID NO:24; PTTPPRPI SEQ ID NO:25; TTPPRPIP, SEQ ID NO:26; TPPRPIPK, SEQ ID NO:27; PPRPIPKP, SEQ ID NO:28; PRPIPKPS, SEQ ID NO:29; RPIPKPSP, SEQ ID NO:30; PIPKPSPW, SEQ ID NO:31; IPKPSPWA, SEQ ID NO:32; PKPSPWAP, SEQ ID NO:33; KPSPWAPK, SEQ ID NO:34; PSPWAPKK, SEQ ID NO:35; SPWAPKKH, SEQ ID NO:36; PWAPKKHR, SEQ ID NO:37; WAPKKHRR, SEQ ID NO:38; APKKHRRL, SEQ ID NO:39; PKKHRRLS, SEQ ID NO:40; KKHRRLSS, SEQ ID NO:41; KHRRLSSD, SEQ ID NO:42; HRRLSSDQ, SEQ ID NO:43; RRLSSDQD, SEQ ID NO:44; RLSSDQDQ, SEQ ID NO:45; LSSDQDQS, SEQ ID NO:46; SSDQDQSQ, SEQ ID NO:47; SDQDQSQT, SEQ ID NO:48; DQDQSQTP, SEQ ID NO: 49; QDQSQTPE, SEQ ID NO:50; DQSQTPET, SEQ ID NO:51; QSQTPETP, SEQ ID NO:52; SQTPETPA, SEQ ID NO:53; QTPETPAT, SEQ ID NO:54; TPETPATP, SEQ ID NO:55; PETPATPL, SEQ ID NO:56; ETPATPLS, SEQ ID NO:57; TPATPLSC, SEQ ID NO:58; PATPLSCC, SEQ ID NO:59; ATPLSCCT, SEQ ID NO:60; TPLSCCTE, SEQ ID NO:61; PLSCCTET, SEQ ID NO:62; LSCCTETQ, SEQ ID NO:63; SCCTETQW, SEQ ID NO:64; CCTETQWT, SEQ ID NO:65; CTETQWTV; SEQ ID NO:66; TETQWTVL, SEQ ID NO 67; ETQWTVLQ, SEQ ID NO:68; TQWTVLQS, SEQ ID NO:69; QWTVLQSS, SEQ ID NO:70; WTVLQSSL, SEQ ID NO:71; TVLQSSLH, SEQ ID NO:72; VLQSSLHL, SEQ ID NO:73; LQSSLHLT, SEQ ID NO:74; QSSLHLTA, SEQ ID NO:75; SSLHLTAH, SEQ ID NO:76; SLHLTAHT; SEQ ID NO: 77; LHLTAHTK, SEQ ID NO:78; HLTAHTKD, SEQ ID NO: 79; LTAHTKDG, SEQ ID NO:80; TAHTKDGL, SEQ ID NO:81; AHTKDGLT, SEQ ID NO:82; HTKDGLTV, SEQ ID NO:83; TKDGLTVI, SEQ ID NO:84; KDGLTVIV, SEQ ID NO:85; DGLTVIVT, SEQ ID NO:86; GLTVIVTL, SEQ ID NO:87; LTVIVTLH, SEQ ID NO:88; and TVIVTLHP, SEQ ID NO:89.
FIG. 1B shows the sequence of the E4 protein from HPV16 (top row, SEQ ID NO:90), HPV1 (bottom row, SEQ ID NO:91) and a consensus sequence (middle row, SEQ ID NO:92), and the binding sites of various antibodies or antigen-binding variants of antibodies.

Sequences are identified as follows: SEQ ID NO: 93; HPV54, SEQ ID NO: 94; HPV32, SEQ ID NO: 95; HPV42, SEQ ID NO: 96; HPV3, SEQ ID NO: 97; HPV28, SEQ ID NO: 98; HPV10, SEQ ID NO:99; HPV29, SEQ ID NO: 100; HPV61, SEQ ID NO:101; HPV2a, SEQ ID NO:102; HPV 27, SEQ ID NO:103; HPV57, SEQ ID NO:104; HPV26, SEQ ID NO:105; HPV30, SEQ ID NO:106; HPV53, SEQ ID NO:107; HPV56, SEQ ID NO:108; HPV66, SEQ ID NO:109; HPV18, SEQ ID NO:110; HPV45, SEQ ID NO:111, HPV39, SEQ ID NO: 112; HPV70, SEQ ID NO: 113; HPV59, SEQ ID NO:114; HPV7, SEQ ID NO: 115; HPV40, SEQ ID NO: 116; HPV16, SEQ ID NO: 117; HPV35, SEQ ID NO: 118; HPV31,SEQ ID NO: 119; HPV52, SEQ ID NO: 120; HPV33, SEQ ID NO: 121; HPV58, SEQ ID NO: 122; RHPV1, SEQ ID NO: 123; HPV66, SEQ ID NO: 124; HPV11, SEQ ID NO: 125; HPV44, SEQ ID NO: 126; HPV55, SEQ ID NO: 127; HPV13, SEQ ID NO: 128; PCPV1, SEQ ID NO: 129; HPV34, SEQ ID NO: 130; HPV19, SEQ ID NO: 131; HPV25, SEQ ID NO: 132; HPV20, SEQ ID NO: 133, HPV21, SEQ ID NO: 134; HPV14d, SEQ ID NO: 135; HPV5, SEQ ID NO: 136; HPV36, SEQ ID NO: 137; HPV47, SEQ ID NO: 138; HPV12, SEQ ID NO: 139; HPV8, SEQ ID NO: 140; HPV24, SEQ ID NO: 141; HPV15, SEQ ID NO: 142; HPV17, SEQ ID NO: 143;

HPV37, SEQ ID NO: 144; HPV9, SEQ ID NO: 145; HPV22, SEQ ID NO: 146; HPV23, SEQ ID NO: 147; HPV38, SEQ ID NO: 148; HPV49, SEQ ID NO: 149; HPV4, SEQ ID NO: 150; HPV65, SEQ ID NO: 151; HPV48, SEQ ID NO: 152; HPV50, SEQ ID NO:153; HPV60, SEQ ID NO:154; BPV1, SEQ ID NO: 155; BPV2, SEQ ID NO:156; EEPV, SEQ ID NO:157; DPV, SEQ ID NO:158; BPV4, SEQ ID NO:159; HPV41, SEQ ID NO:160; COPV, SEQ ID NO:161; CRPV,SEQ ID NO: 162; ROPV, SEQ ID NO: 163; HPV1a, SEQ ID NO: 164; HPV63, SEQ ID NO:165; and MnPV, SEQ ID NO: 166.

DETAILED DESCRIPTION OF THE INVENTION

The method according to the present invention permits the detection, identification and diagnosis of papilloma viruses and papilloma virus infections in organisms susceptible to such infections.

Such organisms are preferably mammals, and most preferably humans. Where the organism is a human organism, the papilloma virus may be a type or types of human papilloma virus (HPV).

The sample of patient's cells may comprise skin cells (e.g. in the case of warts, veruccas and the like, caused by cutaneous HPV infections). Cutaneous lesions, such as those induced by HPV types 5, 8, 14, 17, 20, are difficult to manage clinically, and are often associated with malignancies in imnmunlosuppressed patients (Benton et al, 1992 Papillomavinis Reports 3, 23–26). Alternatively, the sample may comprise mucosal cells, especially cervical cells, In the case of HPV infections of the urinogenital tract. Methods of obtaining and preparinge such samioples for use in the method of the invention are known to those skilled in the art or will be apparent from the present disclosure.

The term "pre-cancerous cervical lesions" is intended to refer to those abnormalities which clinically may be described as "pre-malignant" conditions and which may, without treatment, proceed to full malignancies. As set forth above, such lesions are screened for routinely by, for example, cervical smear testing. The present invention allows for cells obtained from patients by methods such as cervical smears to be tested more accurately and more quickly for HPV infection.

Preferably, the molecule which binds specifically to E4 protein comprises an antibody motecule or an antigen-binding variant thereof, such as an Fab, Fv, scFv, "diabody" and the like. The molecule may comprise monoclonal or polyclonal antibodies, or antigen-binding portions of antibodies selected from libraries by screening (e.g. using phage display technology). Alternatively the molecule may be some other polypeptide, peptide, a synthetic compound or an RNA or DNA aptamer, generated by a procedure such as SELEX. In some preferred embodiments the molecule comprises a label moiety, such as a fluorophore, chromophore, enzyme or radio-label, so as to facilitate monitoring of binding of the molecule to E4 protein. Such labels are well-known to those skilled in the art and include, for example, fluorescein isothiocvanate (FITC), β-galactosidase, horseradish peroxidase, streptavidin, biotin, $^{35}$S or $^{125}$I. Other examples will be apparent to those skilled in the art. The label may in some instances be conjugated to the antibody or antigen-binding variant, or may be present (where the label is a peptide or polypeptide) as a fusion protein.

Preferablly the molecules used in the method of the invention bind selectively to the E4 protein of a certain HPV type or types, but notto the E4 protein of other HPV types. Accordingly, in one embodiment the invention can be used to determine the type or types of HPV infecting a patient. This is very significant, as progression to malignant disease (and hence clinical prognosis) is heavily dependent on HPV type. Accordingly, in a second aspect the invention provides a method of determining the type(s) of HPV infection in a patient, the method comprising the steps of: obtaining a sample of the patient's cells from the site of HPV infection: contacting the cells with a molecule that binds specifically to a subject of HPV E4 proteins; and monitoring said binding.

In the method of the second aspect of the invention, the subset of E4 proteins to which the molecule binds may consist of a single HPV type E4 protein, or may consist of a plurality of E4 proteins of different types, but will not encompass the E4 proteins of all known HPV types, such that binding or non-bindiny (as appropriate) of the molecule to the E4 protein present in the cell sample will allow an investigator to make certain deductions about the identity of the HPV type(s) infecting the patient.

In practice it may be advantageous to employ a plurality of different molecules, which bind to different subsets of E4 proteins. This may be necessary to identify unambiguously the type(s) of HPV infecting the patient, although it may not be essential as a prognostic indicator. For example, the ability to limit the infecting HPV type(s) to a particular subset (or exclude such a subset) may be sufficient. By way of explanation, it is known that mucosal HPV types 6, 11, 42, 43 and 44 are associated with external genital papillomas (condylomata accuminata) which have a low risk of progression to cancer, but are difficult to eradicate and are disruptive to the lives of the patients. The hiher risk mucosal types (31, 33, 35, 51, 52, 58, 61 and 16, 18, 45, 56) cause asymptomatic flat warts (flat concyloma) which can progress to high grade cervical intraepithelial neoplasia (CIN) and cancer. The highest risk of progression to malignancy is associated with lesions caused by HPV types 16, 18, 45 and 56.

Molecules which bind to desired HPV types, but not to undersired HPV types, may be generated for example by randomisation and selection techniques. These include phage display, and other techniques suitable for displaying antibodies or other polypeptides; and procedures for generating nucleic acid binding molecules, for example RNA aptamers, such as SELEX. These procedures are well known to those of ordinary skill in the art and described below for the purposes of exemplification. The invention accordingly provides HPV-binding molecules targetted to the HPV E4 protein, which are useful in methods as described herein.

According to the present invention, E4-binding molecules are preferably targeted to extracellular portions of the E4 polypeptide. Such portions tend to be hydrophilic in character. Preferably, therefore, the E4 binding molecules according to the invention specifically bind to hydrophilic portions of the HPV E4 protein.

The present invention moreover provides a particular region of the E4 protein to which 10 molecules (particularly antibody molecules or variants thereof) may bind with considerable specificity. Although homologous regions exist in all HPV E4 proteins, the region varies in amino acid sequence between HPVs of different types. The region corresponds to a peak of hydrophilicity in the E4 protein and is probably surface-exposed. The region is highly charged (acid/base-rich). In HPV type 16, the amino acid sequence of the region is (from N-terminal to C-terminal) RPIPKPSP-WAPKKHRRLSDQDSQTP (SEQ ID NO: 4). Clearly the amino acid sequence of the E4 proteins of other HPV types will not necessarily be identical to that in type 16, but with the benefit of the present disclosure (e.g. FIG. 9) the corresponding region can readily be identified in other E4 proteins by those skilled in the art by use of conventional alignment and sequence comparison computer programs (about 65 of the 70 or so known HPV genomes have been cloned and sequenced).

Thus, in a third aspect the invention provides an antibody molecule, or an antigen binding variant thereof, which binds specifically to HPV E4 protein in the region of amino acid residues RPIPKPSPWAPKKHRRLSDQDSQTP (SEQ ID NO: 4) of HPV16 E4 protein, or the corresponding hydrophilic, acid/base-rich region of other HPV E4 proteins, preferably other than the antibody TVG 402 identified by Doorbar et al, (1992 Virology 187, 353–359).

Moreover, the invention provides the use of an antibody molecule, or an antigen binding variant thereof, which binds specifically to HPV E4 protein in the region of amino acid residues RPIPKPSPWAPKKHRRLSDQDSQTP (SEQ ID NO: 4) of HPV16 E4 protein, or the corresponding hydrophilic, acid/base-rich region of other HPV E4 proteins for the detection of HPV infections as described herein.

Figure 9:
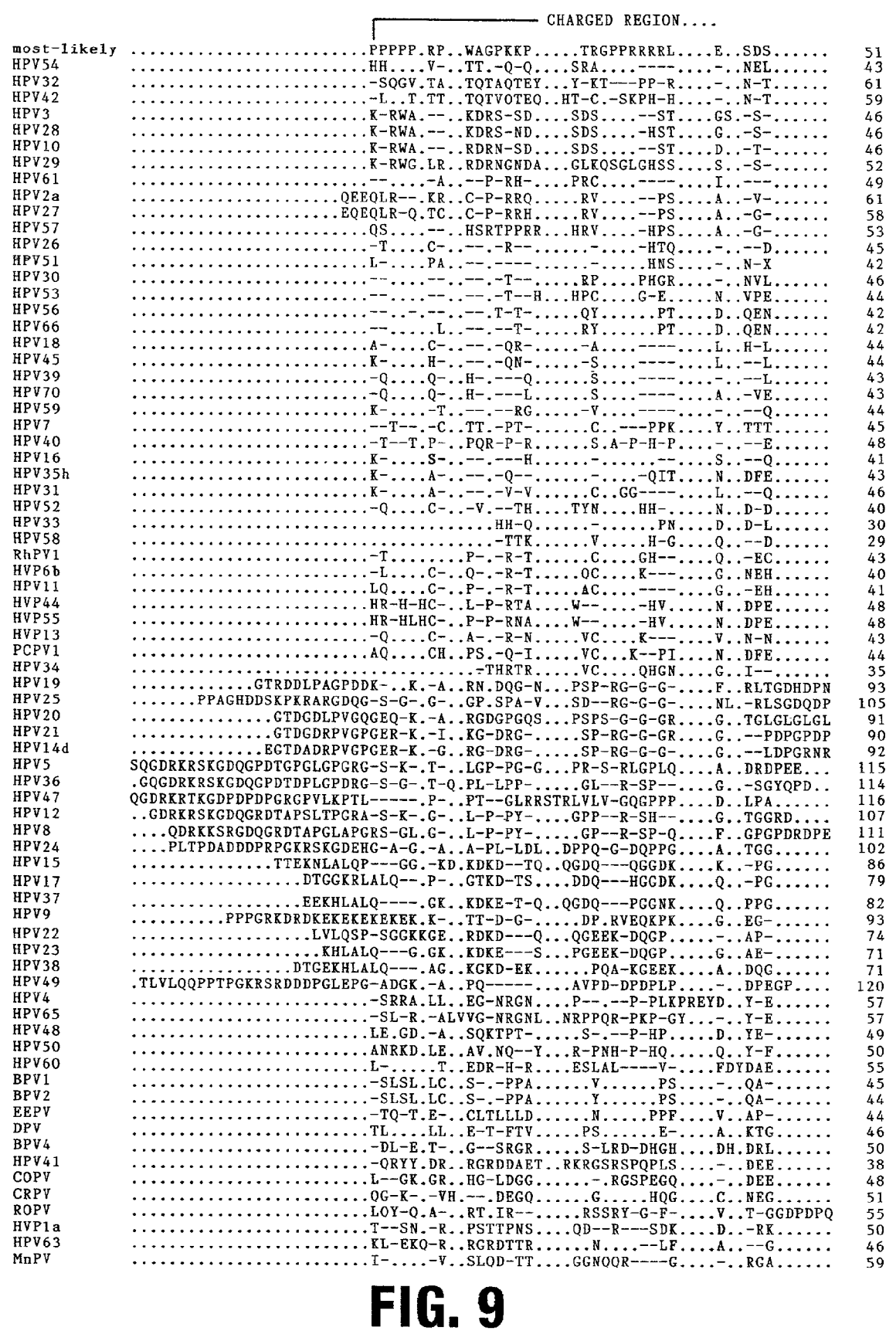

The corresponding hydrophilic acid/base-rich regions of large numbers of different HPV types are shown in FIG. 9. FIG. 9 shows a consensus-type amino acid sequence ("most likely") on the top row, with the sequence of HPV E4 proteins below. Dots indicate gaps introduced to facilitate the alignment, dashes denote amino acid residue matches with the consensus sequence. Numbering on the right hand side of the figure indicates the number of amino acid residues from the actual or predicted E1^E4 splice site. It will be appreciated by those skilled in the art from the aligrment that whilst the hydrophilicity of the reaion is conserved amongst different HPV types, the actual amino acid sequence varies quite considerably, such that reagents binding to this region may be expected to be highly HPV type-specific.

Preferably the antibody of the invention has a binding site, as identified by the SPOTS epitope mapping system within the region. RPIPKPSPWAPKKHR (SEQ ID NO: 167) (or the corresponding amino acid sequence from other HPV types). A particularly preferred molecule is the Fab fragment TVG405, described further below, which binds to the epitope PKPSPWAPKKH(R) (SEQ ID NO: 168) with extremely high affinity and is of particular usefulness in the methods of the invention defined above.

The arginine residue indicated in brackets at the C-terminal of the TVG405 epitope is not essential for high affinity binding.

The Fab fragment TVG405 was isolated by the present inventor using phage display technology, as described below. Those skilled in the art will understand that different antibodies or Fab fragments may readily be obtained by using similar phage display techniques (and screening with E4 proteins or portions thereof), or by using more conventional immunisation techniques (e.g. immunising mice, rabbits, rats or the like with E4 protein or peptides corresponding to portions of the E4 protein) to obtain polyclonal antisera or monoclonal antibodies (using well known hybridoma techniques of Milstein et al). Complete antibody molecules can readily be prepared from Fab—encoding sequences (e.g. isolated by phage display techniques) using standard DNA manipulation techniques described by Sambrook et al, (Molecular Cloning: A Laboratory Manual, 2nd Edition, Cold Spring Harbor Laboratory Press, NY, USA) to join appropriate DNA sequences.

Similarly, standard DNA manipulative techniques can be used to modify DNA sequences encoding anti-E4 antibodies or antigen-binding variants thereof. In particular site-directed mutagenesis or PCR can be used to modify the coding sequences, so as to produce modified anti-E4 antibodies with different binding specificities or affinities. Alternatively fusion proteins, comprising the E4-binding site of an Fab, Fv or antibody and the like, may be prepared.

Molecules capable of binding E4 may be used as antiviral or anti-cancer agents, or parts of such agents. For example, antibody molecules or E4-binding peptide as described above may be employed for this purpose. Preferably, however, the E4 protein and/or molecules capable of binding thereto may be used to design E4-binding molecules, preferably small molecules, by rational drug design.

Such a process preferably involves the crystallisation of E4 or a molecule capable of binding thereto. More preferably, such a process involves the co-crystallisation of E4 and a binding agent. Such a procedure gives information concerning the interaction between E4 and the binding molecule, which can be used to design small molecules capable of mimicking the binding interaction.

Crystallisation involves the preparation of a crystallisation buffer, for example by mixing a solution of the peptide or peptide complex with a "reservoir buffer", preferably in a 1:1 ratio, with a lower concentration of the precipitating agent necessary for crystal formation. For crystal formation, the concentration of the precipitating agent is increased, for example by addition of precipitating agent, for example by titration, or by allowing the concentration of precipitating agent to balance by diffusion between the crystallisation buffer and a reservoir buffer. Under suitable conditions such diffusion of precipitating agent occurs along the gradient of precipitating agent, for example from the reservoir buffer having a higher concentration of precipitating agent into the crystallisation buffer having a lower concentration of precipitating agent. Diffusion may be achieved for example by vapour diffusion techniques allowing diffusion in the common gas phase. Known techniques are, for example, vapour diffusion methods, such as the "hanging drop" or the "sitting drop" method. In the vapour diffusion method a drop of crystallisation buffer containing the protein is hanging above or sitting beside a much larger pool of reservoir buffer. Alternatively, the balancing of the precipitating agent can be achieved through a semipermeable membrane that separates the crystallisation buffer from the reservoir buffer and prevents dilution of the protein into the reservoir buffer.

In the crystallisation buffer the peptide or peptide/binding partner complex preferably has a concentration of up to 30 mg/ml, preferably from about 2 mg/ml to about 4 mg/ml.

Formation of crystals can be achieved under various conditions which are essentially determined by the following parameters: pH, presence of salts and additives, precipitating agent, protein concentration and temperature. The pH may range from about 4.0 to 9.0. The concentration and type of buffer is rather unimportant, and therefore variable, e.g. in dependence with the desired pH. Suitable buffer systems include phosphate, acetate, citrate, Tris, MES and HEPES buffers. Useful salts and additives include e.g. chlorides, sulphates and further salts specified in Example 1. The buffer contains a precipitating agent selected from the group consisting of a water miscible organic solvent, preferably polyethylene glycol having a molecular weight of between 100 and 20000, preferentially between 4000 and 10000, or a suitable salt, such as a sulphates, particularly ammonium sulphate, a chloride, a citrate or a tartrate.

A crystal of E4 itself or an E4-derived peptide, or E4 (peptide)/binding partner complex according to the invention may be chemically modified, e.g. by heavy atom derivatization. Briefly, such derivatization is achievable by soaking a crystal in a solution containing heavy metal atom salts, or a organometallic compounds, e.g. lead chloride, gold thiomalate, thimerosal or uranyl acetate, which is capable of diffusing through the crystal and binding to the surface of the protein. The location(s) of the bound heavy metal atom(s) can be determined by X-ray diffraction analysis of the soaked crystal, which information may be used e.g. to construct a three-dimensional model of the peptide.

A three-dimensional model is obtainable, for example, from a heavy atom derivative of a crystal and/or from all or part of the structural data provided by the crystallisation. Preferably building of such model involves homology modelling and/or molecular replacement.

The preliminary homology model can be created by a combination of sequence alignment with any of the E4 proteins the sequence of which is known, secondary structure prediction and screening of structural libraries. For example, the sequences of HSV 16 and 34 E4 can be aligned as set forth herein.

Computational software may also be used to predict the secondary structure of E4 peptides or peptide complexes. The peptide sequence may be incorporated into the E4 structure. Structural incoherences, e.g. structural fragments around insertions/deletions can be modelled by screening a structural library for peptides of the desired length and with a suitable conformation. For prediction of the side chain conformation, a side chain rotamer library may be employed.

The final homology model is used to solve the crystal structure of E4 or peptides thereof by molecular replacement using suitable computer software. The homology model is positioned according to the results of molecular replacement, and subjected to further refinement comprising molecular dynamics calculations and modelling of the inhibitor used for crystallisation into the electron density.

Similar approaches may be used to crystallise and determine the structure of E4-binding polypeptides, including antibodies and antibody fragments, for example those provided by the present invention.

It has surprisingly been found that E4 expression correlates strongly with vegetative DNA replication in HPV-infected cells, making detection of E4 expression a particularly appropriate indicator of HPV infection, and thus particularly useful in screening for precancerous cervical lesions.

Present available methods of cervical screening by HPV detection are based on DNA hybridisation. They involve cell lysis or permeabilisation and are performed in an ELISA-type 96 well format. The hybridisation is ultimately visualised as a colour change in one of the wells.

Although the antibodies of the present invention could be used in a similar way (i.e. following cell lysis), they are amenable to a quicker procedure which would be more readily carried out routinely by histopathology laboratories. Samples comprising cervical cells may be taken as usual. These are be spread for example on a microscope slide or other support using techniques known in the art, for example as exemplified herein, and stained with, for example, an anti-E4 Fab. Detection may be performed with a secondary antibody-enzyme conjugate (horseradish peroxidase, alkaline phosphatase), or the Fab could be directly conjugated, for example to a fluorophore, such as FITC. This approach may be adapted for use with systems that are currently available for increasing the sensitivity of antibody detection. At present, cervical smears are examined routinely by microscopy. The proposed approach would require no new equipment and could easily fit around existing methods.

It is envisaged that the standard method of detection may be modified. Antibody binding may be carried out while the cells are in suspension, with cells being spun down prior to analysis. This would improve the quality of the screen.

Considerable effort in diagnosis is aimed at automating screening methods. The use of antibodies or antigen-binding variants thereof for HPV detection greatly facilitates this.

In summary, it has been shown that:
1. The E4 protein can be detected in productively infected HPV-induced lesions, and in low and high grade cervical neoplasia even when differentiation of the infected keratinocyte is insufficient to support production of capsid proteins and assembly of infections virions.
2. E4 expression correlates closely with vegetative viral DNA replication indicating that detection of the E4 protein is as efficient as detection of viral DNA replication for the detection of virus infection.
3. The E4 protein is abundant in the upper layers of infected tissue and is thus detectable in cells taken during routine smear tests.

The invention will now be described by way of illustrative examples.

EXAMPLE 1

Preparation of Anti-E4 Monoclonal and Polyclonal Immunoglobulins

Although Mabs against HPV16 E1^E4 have been described previously (TVG401, 402, 403; Doorbar et al, 1992) these reagents recognise a single overlapping epitope at the major antigenic site of E4, and have been reported not to detect the protein in archival tissue biopsies (Doorbar et al, 1992).

Although these results suggest that E4 may not be a candidate for immunological detection of HPV, further antibodies are generated targeted at the N and C termini of HPV16 E4.

The generation of further Mabs by standard hybridoma technology results in the isolation of TVG404, an IgM which recognises an epitope at the very C-terminus of the protein.

To complement this reagent polyclonal antiserum to the N-terminus of the protein is raised against an N-terminal synthetic peptide (–E4 N term). Polyclonal antibodies (to HPV16 and HPV63 E4 proteins) are prepared by immunisation of rabbits with maltose binding protein E4 fusion protein (MBP-E4). Antibody titres are monitored in ELISA using purified glutathione S transferase E4 fusion protein (GST-E4).

Antibodies to the N-terminus of the protein are raised against the synthetic peptide MADPAAATKYPLC (SEQ ID NO: 169) after conjugation to thyroglobulin or keyhole limpet haemocyanin through its C-terminal cysteine residue. Conjugation is carried out using m-Maleimidobenzoyl-N-hydroxysuccinimide ester (MBS) as described by Green et al (1982).

Antibody specificities are confirmed by epitope mapping, as follows: the HPV 16 E4 protein is synthesised as a series of 85 overlapping octamers (single amino acid overlap) by solid phase fmoc chemistry using the SPOTS epitope mapping system (Genosys Biotechnologies, Cambridge, UK).

Accuracy of synthesis is confirmed using the HPV16 E1^E4 monoclonal TVG402 which binds the major antigenic site of the protein (Doorbar et al, 1992). Filters are regenerated as described by the manufacturers and antibody binding is visualised by ECL (Amersham, Little Chalfont, UK). Polyclonal serum is used at 1/250 dilution, purified Fabs at approximately 1 g/ml, and hybridoma supernatant at 1/10 dilution.

In FIG. 1A the sequences of the 85 overlapping E4 synthetic peptides are shown at the top of the figure, and the results of the epitope mapping experiments are shown below. The dark spots represent binding of the antibody to the synthetic peptide shown above it. Only the portion of the filter containing peptides which react with each antibody are shown.

In FIG. 1B, the locations of epitopes on the E1^E4 amino acid sequence are summarised above the HPV16 sequence. Alignment with a consensus E4 sequence prepared by comparison of 70 putative E1^E4 sequences (Doorbar and Myers, 1996b) is shown beneath the sequence of HPV16 E1^E4, and the sequence of the HPV1 E1^E4 protein is shown beneath this. The binding sites of the existing HPV1 E1^E4 Mabs (Doorbar et al, 1988) are shown beneath the HPV1 sequence. The proteolytic cleavage sites that give rise to the 16K and 10/11K gene products in the E1^E4 protein of HPV1 (Doorbar et al, 1988; Roberts et al, 1994) are indicated beneath the HPV1 sequence allowing prediction of putative sites in the E1^E4 sequence of HPV16.

EXAMPLE 2

Preparation of Synthetic Immunoglobulins

Fabs are isolated from a synthetic antibody displayed on fd bacteriophage (Griffiths et al, 1994) as described below. Immunotubes (Life Technologies, Paisley, UK) are coated overnight at 4° C. with either MBP-E4 or GST-E4 at a concentration of 0.1 g/ml. These are subsequently blocked at 37° C. for 1 hour in PBS/2% marvel™ prior to incubation in the presence of $10^{11}$ phage on a blood tube rotator (37° C.). Unbound phage are poured off and tubes are washed 10× with PBS/0.1% Tween 20. Binders are eluted with 100 mM triethylamine pH 11.0 (1 ml) and immediately neutralised with 1M Tris (pH8.0) before being reintroduced into E. coli TG1 cells. The enriched library is grown up and the selection procedure repeated three more times.

Phage selections are carried out alternately against GST 16 E1^E4 and MBP 16 E1^E4 in order to prevent isolation of antibodies to MBP or GST protein, using a repertoire of $6.5 \times 10^{10}$ (Griffiths et al, 1994). MBP 16 E4 is expressed at higher levels (>50 mg/litre of bacteria) than the GST fusion (approx. 5 mg/litre of bacteria) but, in any event, antibody isolation requires as little as 1 g of antigen (Hawkins et al, 1992). Phage displaying antibodies with affinity for E4 are identified by ELISA (against GST-E4, MBP-E4, GST and MBP), and activity is confirmed by phage western blotting. Immunoglobulin genes are transferred from the isolated phage into the bacterial expression vector pUC119.His.myc (Griffiths et al 1994) and soluble Fabs are purified from the periplasmic space of induced bacteria by Nickel-NTA chromatography (Qiagen, Crawley UK). Antibody titres are established by ELISA.

After four rounds of selection, individual clones are examined for their ability to bind either E1^E4, unfused GST or MBP, or bovine serum albumin (BSA). 47 clones (out of 100) are able to bind MBP 16 E1^E4, of which 39 could also bind GST 16 E4. None of these clones interacted with BSA, GST or MBP. BstNI fingerprinting (Marks et al, 1992: Nissim et al, 1994) revealed three distinct Fabs amongst these clones, and their immunoglobulin genes are subcloned into the prokaryotic expression vector pUC119His.6myc to allow the production of soluble anti-E4 Fabs (Griffiths et al, 1994). Approximately 5 mg (per liter of bacteria) of anti-E4 Fab (TVG 405, 406 and 407) can be extracted from the periplasmic space of induced bacteria and all are found to specifically detect E1^E4 by ELISA and western blotting. Fab TVG 407 binds an epitope which is identical to that recognised by the hybridoma-derived Mab, TVG 409 (FIG. 1). The remaining synthetic Fabs recognise novel epitopes upstream (TVG 405) or downstream (TVG 407) of this major antigenic region of E4 and the results are summarised in FIG. 1.

It is found that the amino acid sequence of the CDR3 loops of the TVG 405 and TVG 407 Fabs are as follows:

| | |
|---|---|
| TVG 405 | heavy chain CDR3 sequence: LLRGAFDY (SEQ ID NO: 170) |
| | light chain CDR3 sequence: NSRDSSGGNAV (SEQ ID NO: 171) |
| TVG 407 | heavy chain CDR3 sequence: LVQGSFDY (SEQ ID NO: 172) |
| | light chain CDR3 sequence: QADSSTHV (SEQ ID NO: 173) |

Measurement of Antibody Affinity

Affinities of synthetic (TVG405, TVG406 and TVG407), and hybridoma-derived Fabs (TVG402) are analysed by surface plasmon resonance using a BIAcore 2000 instrument (Pharmacia Biosensor, St. Albans, UK) as described by the manufacturer. MBP-E4 aggregates are dissociated under reducing conditions in 0.5% SDS, 1 mM β-mercaptoethanol, 50 mM $Na_2CO_3$/$NaHCO_3$ (pH 8.5) and biotinylated using NHS-LC-biotin (Sigma, St Louis, USA; 25 mg/ml in DMSO) at a biotin:protein molar ratio of 6:1 (Johnson et al, 1991). Monomeric MBP-E4 is recovered by FPLC chromatography using a Superdex S200 HR10/30 column run in 6M Urea/1 mM β-mercaptoethanol/PBS/0.2 mM EDTA (pH7 2), before being bound to a streptavidin-coated sensor chip and "refolded" in vitro in PBS/0.2 mM EDTA/0.1 mg/ml protease-free BSA (Sigma). Fabs are isolated from purified TVG402 using an Immunopure Fab kit (Pierce, Rockford, USA), and monomeric preparations are obtained by FPLC gel chromatography (Superdex S200 HR10/30 column run in PBS/0.2 mM EDTA (pH 7.2)) Sensor chip surfaces are regenerated using 6M urea column buffer (described above). On and off rates are derived by non linear curve fitting using the proprietary 'BIAanalysis' software.

Binding activities are in the order of 20% of total protein levels for the bacterially-derived antibodies, and 50% for Fabs derived from hybridoma culture supernatant. The affinities of TVG405 and TVG402 are calculated from on- and off-rates obtained by non-linear curve fitting to sets of BIAcore binding curves.

Figure 2:
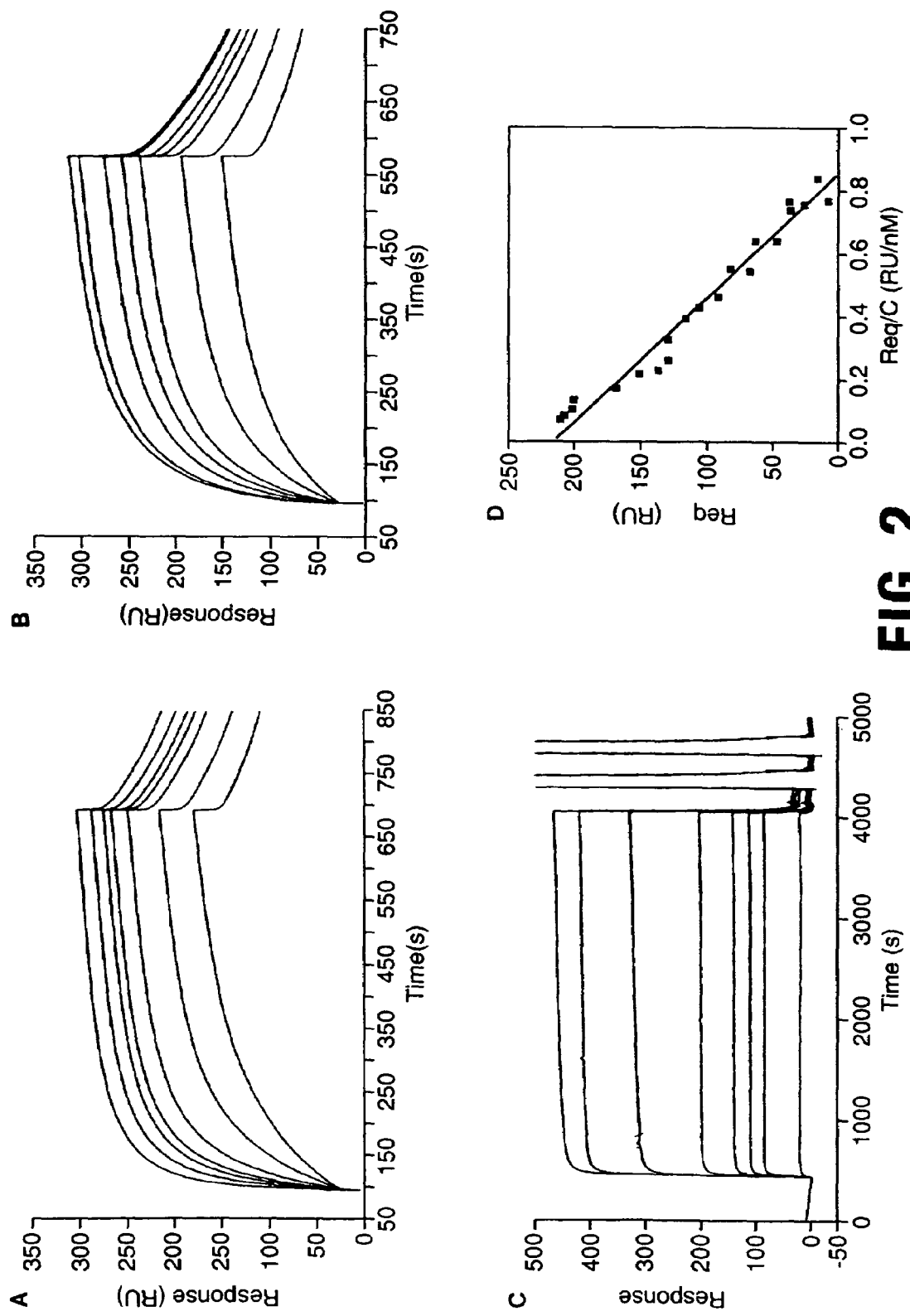
FIGS. 2A–2D show four sensograms (arbitrary response units against time in seconds) obtained using surface plasmon resonance apparatus.

FIG. 2A shows an overlay of binding curves (sensograms) obtained after passing Fab TVG405 over a BIAcore chip coated with MBP-E4 fusion protein as described above. Fab concentrations range from 10 mM (lowest curve) to 300 nM (upper curve) through 5 intermediate dilutions. The extent of binding is indicated in resonance units on the X-axis, against time in seconds on the Y-axis. Purified Fab is injected at around 100 seconds and washing initiated at 700 seconds. The affinity ($K_d$) of TVG405 is calculated as between 0.3 and 1.25 nM by analysis of the association and dissociation curves using BIAevaluation software (Pharmacia, UK).

FIG. 2B shows an overlay of binding curves (as described above) for the hybridoma-derived Fab TVG402 over a concentration range 100 nM to 1 M. The $K_d$ is estimated as 70 nM.

TVG405 has an association rate constant ($k_{on}$) of $1.8 \times 10^6$ $M^{-1}.s^{-1}$ and an off rate ($k_{off}$) of $2 \times 10^3$ $s^{-1}$ indicating a molar dissociation constant (Kd) of approximately 1 nM. The best hybridoma-derived antibody—TVG402—has an affinity of only 70 nM, and had a $k_{on}$ of $4.2 \times 10^4$ $M^{-1}.s^{-1}$ and a $k_{off}$ value of $3 \times 10^3$ $s^{-1}$. TVG 406 and 407 displayed rapid kinetics and are thus examined by Scatchard analysis of equilibrium binding data, as shown for TVG407.

FIG. 2C shows the equilibrium binding curve of Fab TVG407, which displays rapid kinetics. FIG. 2D shows Scatchard analysis of the data presented in FIG. 2C using BIAevaluation software. Equilibrium values are corrected for bulk refractive index changes by subtracting values from a surface blocked with biotin, from the values shown in FIG. 2C. In the plot shown the slope is—$K_d$ and the Y-axis intercept is '$R_{max}$', i.e. the binding level at saturation with Fab. The uncorrected $K_d$ values for TVG407 and TVG406 are 250 nM and 140 nM which, when the activity of the Fab preparation is considered, indicates actual affinities of 50 nM and 28 nM.

TVG407 has an affinity (Kd) of 50 nm after correction for biological activity, and TVG406 has an affinity (Kd) of 28 nM. The amino acid sequence of the heavy and light chain CDR3 loops are established by DNA sequencing, further confirming that the three antibodies are distinct.

EXAMPLE 3

Preparation of Anti-E4 Peptides

A commercially available two-hybrid screening kit is purchased from ClonTech and employed for identifying naturally occurring E4-binding peptides, according to the instructions given by the manufacturer. A HeLa cDNA library, obtained from the same supplier, is screened. By this method, seven DNA sequences are isolated which encode E4-binding polypeptides, of which three are identified after sequencing.

The first peptide is ferritin. (SEQ ID NO: 1)

The second peptide is a keratin filament binding protein, which has the sequence set forth in (SEQ ID NO: 2).

The third polypeptide is a novel polypeptide recognised as a member of the DEAD box family of proteins, which contain the characteristic sequence motif DEAD (SEQ ID NO: 129). The sequence of the third polypeptide is shown in (SEQ ID NO: 3).

In order to identify the site of interaction between these polypeptides and E4, a series of overlapping peptides of between 10 and 20 amino acids in length is generated by PCR and displayed on phage as described above. The binders are subsequently employed as screening agents to identify HPV16 in mucosal lesions.

EXAMPLE 4

Preparation of Anti-E4 RNA Oligonucleotides

RNA oligonucleotides, known as aptamers, which are capable of specific binding to target molecules can be generated by selection procedures such as SELEX. The SELEX method involves selection of nucleic acid aptamers, single-stranded nucleic acids capable of binding to a desired target, from a library of oligonucleotides. Starting from a library of nucleic acids, preferably comprising a segment of randomised sequence, the SELEX method includes steps of contacting the library with the target under conditions favourable for binding, partitioning unbound nucleic acids from those nucleic acids which have bound specifically to target molecules, dissociating the nucleic acid-target complexes, amplifying the nucleic acids dissociated from the nucleic acid-target complexes to yield a ligand-enriched library of nucleic acids, then reiterating the steps of binding, partitioning, dissociating and amplifying through as many cycles as desired to yield highly specific, high affinity nucleic acid ligands to the target molecule.

DNA Oligonucleotide Library

DNA oligonucleotides 73 bases in length, having a randomised portion of 26 bases, are used for the development of an aptamer capable of binding E4. A library of synthetic RNA oligonucleotides having the following structure is prepared:

```
5' CCTGTTGTGAGCCTCCTGTCGAA(26N)TTGAGCGTTTATTCTTGTC
                                    TCCC 3' (SEQ ID NO: 174)
```

Where N stands for any possible base in the random region. The random region is generated by using a mixture of all four nucleotides (ratio 6:5:5:4, A:C:G:T, to allow for differences in coupling efficiency) during the synthesis of each nucleotide in that stretch of the oligonucleotide library. The resulting complexity is theoretically $4^{26}$ molecules. The scale of synthesis (0.1 µmol) followed by gel purification yields 8.8 nmol which puts an absolute upper limit of approximately $5 \times 10^{15}$ on the number of different molecules actually present.

PCR Amplification with a 5' primer that introduces the recognition site for T7 RNA Polymerase (5' TAATAC-GACTCACTATAGGGAGACAAGAATAAACGCTCAA 3') (SEQ ID NO: 175) and 3'primer (5' GCCTGTTGT-GAGCCTCCTGTCGAA 3') (SEQ ID NO: 176) results in the following template for transcription:

```
5' TAATACGACTCACTATAGGGAGACAAGAATAAACGCTCAA (26N)
TTCGACAGGAGGCTCACAACAGGC 3' (SEQ ID NO: 177)
```

The RNA transcript itself has the following sequence:

```
5' GGGAGACAAGAAUAAACGCUCAA (26N) UUCGACAGGAGGCUCAC
                                  AACAGGC 3' (SEQ ID NO: 178)
```

Anti-E4 aptamers are selected using a conventional SELEX procedure as described in U.S. Pat. No. 5,270,163. Each round consists of the following steps:

1) Selection. The RNA and E4 protein are mixed, incubated at 37° C., washed through a nitrocellulose filter, and RNA is eluted from the filters.
2) Amplification. The RNA eluted from filters is extended with AMV reverse transcriptase in the presence of 50 picomoles of 3' primer in a 50 µl reaction under conditions described in Gauss et al. (1987). To the resulting cDNA synthesis 50 picomoles of 5' primer is added and in a reaction volume of 100 µl and amplified with Taq DNA polymerase as described in Innis (1988) for 30 cycles.
3) Transcription. In vitro transcription is performed on the selected amplified templates as described in Milligan et al. (1987), after which DNaseI is added to remove the DNA template. The resultant selected RNA transcripts are then used in step 1 of the next round. Only one-twentieth of the products created at each step of the cycle are used in the subsequent cycles so that the history of the selection can be traced. The progress of the selection method is monitored by filter binding assays of labeled transcripts from each PCR reaction. After the fourth round of selection and amplification, the labeled selected RNA products produce binding to E4. The binders are used in the detection of HPV in cells derived from cervical smears.

EXAMPLE 5

Detection of HPV in Cutaneous and Mucosal Lesions

Figure 3:
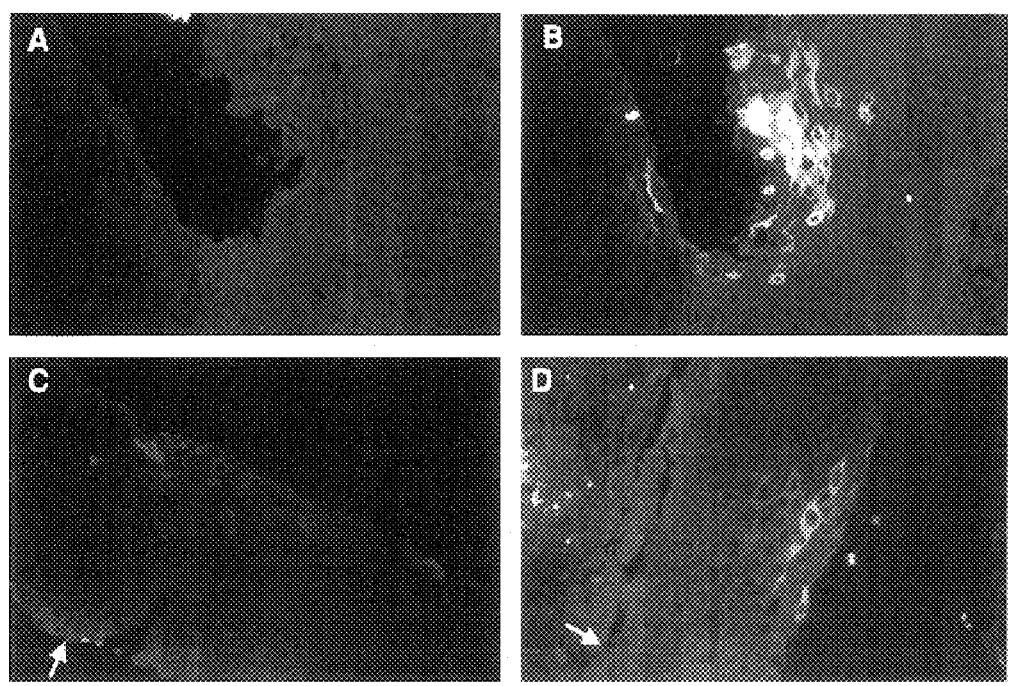
FIGS. 3(A–D) show the use of synthetic Fabs to localize HPV16 E4 protein in vivo by immunostaining of a low-grade HPV16 CIN I. p FIGS. 4(A–I) show the results of staining for L1, HPV16 E4, HPV63 E4, and DAPI, in low-grade HPV16-induced lesion (CIN I), high grade HPV16-induced lesion (CIN II/III), and a section through a verruca caused by HPV63.

All the synthetic Fabs detect the HPV16 E1^E4 protein in formalin fixed paraffin-embedded tissue, although TVG405 consistently show the highest level of staining (FIG. 3).

FIG. 3 illustrates the use of synthetic Fabs to localise HPV16 E4 protein in vivo by immunostaining of a low grade HPV16 CIN I with Fab NIP-C11(Griffiths et al, 1994), which has no reactivity towards HPV16 E4 (FIG. 3A), and the E4-specific Fab TVG405 which is described here (FIGS. 3B, C, D). Fabs are detected using 9E10 as secondary antibody followed by anti-mouse FITC conjugate. E4 is detectable in the upper layers of the epidermis but at greatly varying levels between different lesions with often only a few positive cells being apparent (C, D). The position of the basal layer is arrowed in C and D. Magnification is 200×.

Figure 4:
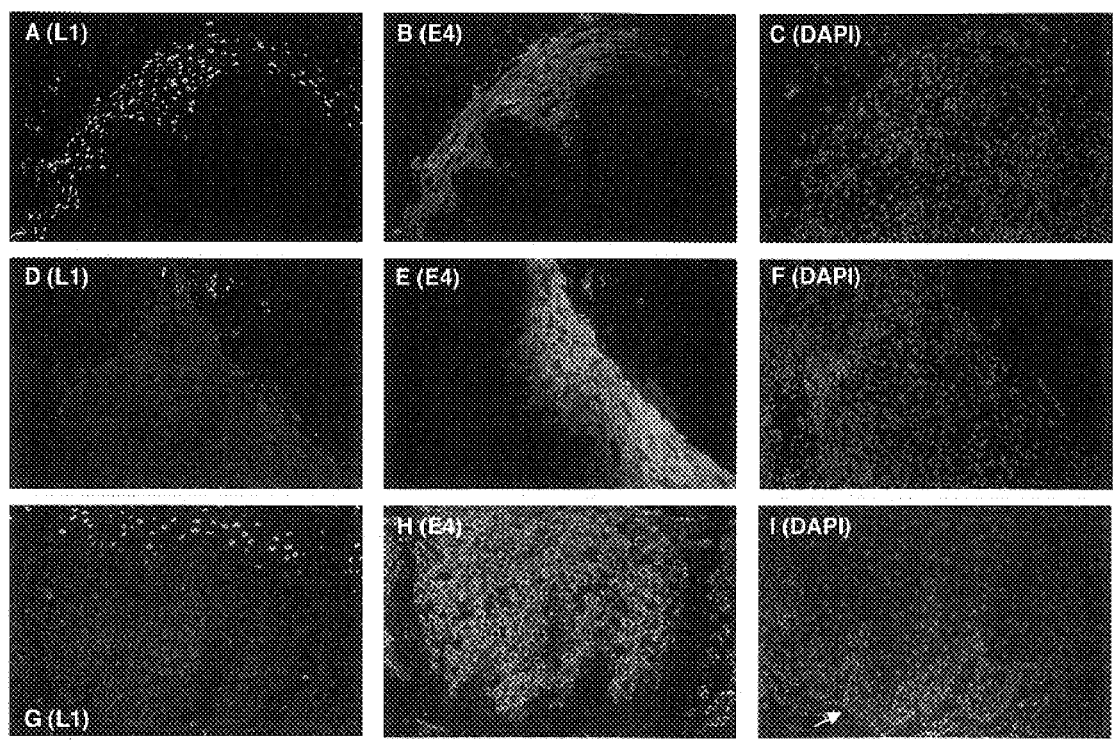

Epitope exposure by microwave treatment enhances the sensitivity of E4 detection, and even allows staining using TVG402 (Doorbar et al, 1992). The extent of E4 expression varies greatly between different lesions (8 HPV16-associated CIN1 biopsies are examined), ranging from expression only in rare cells scattered throughout the biopsy (FIG. 3), to widespread distribution throughout the most differentiated layers of the epidermis (FIG. 4), comparable to the distribution of E4 in cutaneous warts caused by HPV1 and HPV63 where the production of infections virions is also high (FIG. 4). In low grade cervical intraepithelial neoplasia (CIN 1) caused by HPV16, E4 and L1 levels are also found to correlate closely, although expression of the two proteins is not coincident (as previously suggested (Brown et al, 1994). E4 expression precedes the synthesis of the major capsid protein by several cell layers (as revealed by double staining, see FIG. 4) and in high grade cervical lesions (CIN 2/CIN 3) E4 is often abundant, even though the expression of L1 is no longer supported (FIG. 4). This time delay between the commencement of E4 synthesis and the assembly of infectious virions is most apparent in HPV63, where E4 expression coincided with migration of an infected basal cell into the parabasal layers, while expression of L1 is restricted to a narrow strip of cells in the upper granular layer.

FIG. 4 demonstrates that synthesis of E4 is not directly linked to the expression of capsid proteins in high and low grade HPV16 lesions, and benign warts. FIG. 4 shows the results of triple staining using anti L1 antisera (FIGS. 4A, D, G), HPV16 E4 Fab TVG405 (FIGS. 4B and 4E), polyclonal antisera to HPV63 E4 (FIG. 4H), and with DAPI (FIGS. 4C, F, I). A, B and C represent a low grade HPV16-induced lesion (CIN I). D, E and F represent a high grade HPV16-induced lesion (CIN II/III). G, H and I represent a section through a verruca caused by HPV63. In all cases E4 expression precedes L1 expression although by only a few cell layers in CIN I (A, B). In the CIN II/III we assume that terminal differentiation is insufficient to support synthesis of virion structural proteins (D) although E4 expression is abundant (E). The contrast between the onset of E4 expression and the detection of virus structural proteins is most apparent in cutaneous verrucas caused by HPV63 (G, H). The basal layer is indicated by an arrow on the DAPI-stained images. Magnification is 100×.

Onset of Vegetative Viral DNA Replication and Expression of E4 Coincide

Figure 5:
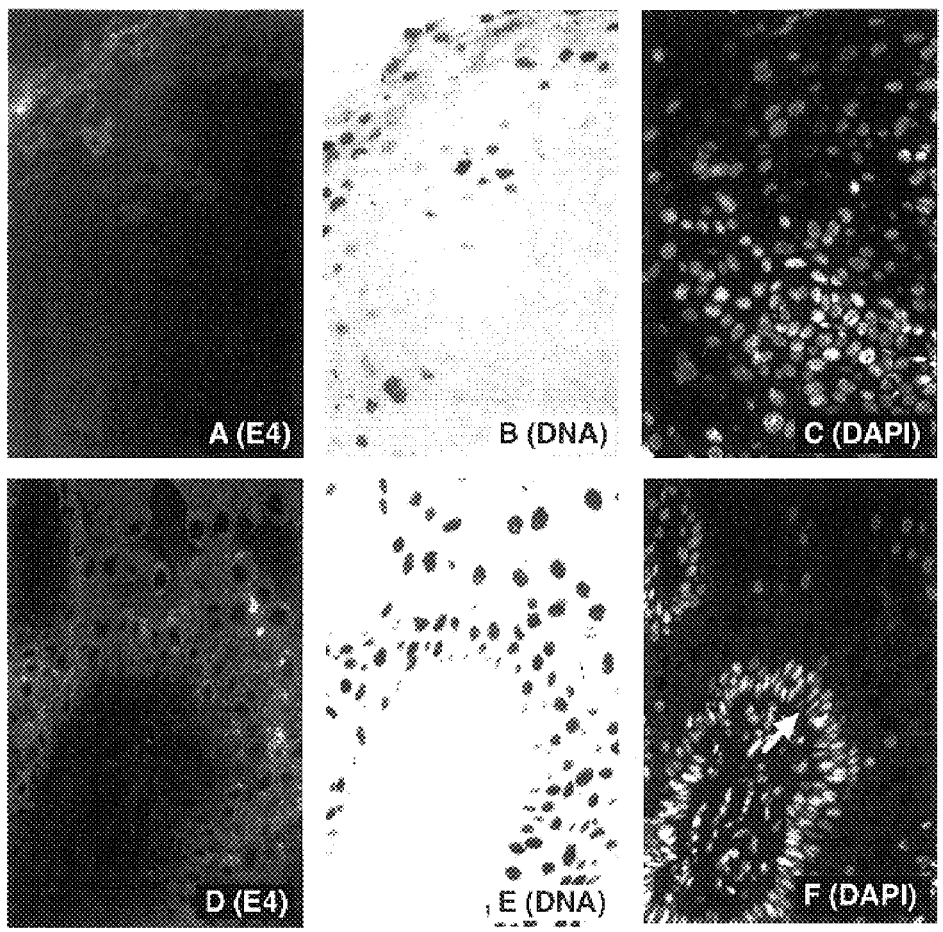
FIGS. 5(A–F) show the results of staining for HPV16 E4 and biotinylated DNA probe, in low grade HPV16 lesions and in benign cutaneous warts.

Vegetative viral DNA replication is found to begin in cells of the mid spinous layer and to correlate exactly with the onset of E4 expression (FIG. 5).

FIG. 5 demonstrates that onset of vegetative viral DNA replication coincides with E4 expression in low grade HPV16 lesions and in benign cutaneous warts. The figure shows triple staining using the HPV16 E4 antibodies TVG402, 405 and 406 (FIG. 5A) and HPV1 E4 antibodies 4.37 and 9.95 (FIG. 5D), biotinylated DNA probe (FIG. 5B—HPV16. FIG. 5E—HPV1), or DAPI (FIGS. 5C and F). A, B and C represent a section through an HPV1-induced CIN I, and D, E and F represent a section through an HPV1-induced verruca. In the HPV16 CIN I, vegetative viral DNA replication and E4 synthesis correlate in the mid to upper layers of the epidermis (A, B). In cutaneous lesions the two events are initiated as soon as the infected cell leaves the basal layer (D, E). Basal cells are illustrated in the DAPI counterstained image (F). Magnification is 200×.

In HPV 1-induced warts vegetative viral DNA replication and E4 synthesis commence much earlier, and are evident immediately after the infected basal cell migrates into the superficial layers (FIG. 5). Only a proportion of the differentiating cells are permissive for vegetative viral DNA replication, and only in these cells is E4 detectable. Neighbouring cells showed neither late gene expression nor vegetative viral DNA replication, suggesting that onset of the two events is closely linked. Although the sensitivity of DNA and E4 detection is not established, these 'normal' cells are likely to be either non-permissive for viral replication or be uninfected. This precise correlation between E4 expression and the onset of vegetative viral DNA replication is also seen in cutaneous warts caused by HPV63 and 65, and in common warts caused by HPV2.

Cells Undergoing Late Gene Expression Show an Abnormal Pattern of Terminal Differentiation when Compared to Non-permissive or Uninfected Cells Cells supporting the late stages of HPV infection can thus be identified by immunostaining with Fab TVG405 (for HPV16) Mab 4.37 (for HPV1) or polyclonal antisera to E4 (HPV63). In warts caused by HPV1, E4-positive cells lack detectable levels of filaggrin or involucrin (FIG. 6(i)). Non-permissive (or uninfected) cells in the same lesion which show neither E4 expression nor vegetative viral DNA replication. express filaggrin and loricrin at levels indistinguishable from those in the surrounding epidermis. Correlation of E4 synthesis with the differentiation-specific keratins K4 and K13 reveals an identical pattern of inhibition. The intensity of K4 and K13 staining is always lower in E4-positive cells than in neighbouring cells that are not expressing E4 (FIG. 6(ii)). K5 and 14, which are present in the basal and lower parabasal cells, are unaffected. This interference with the detection of expression differentiation-specific keratins (K1 and K10 in cutaneous skin) is also apparent in cutaneous warts caused by HPVI (FIG. 6(ii)) but is not evident in warts caused by HPV63 (FIG. 6(ii)). The E4 protein of HPV63 is most closely related to that of HPV1.

Figure 6I:
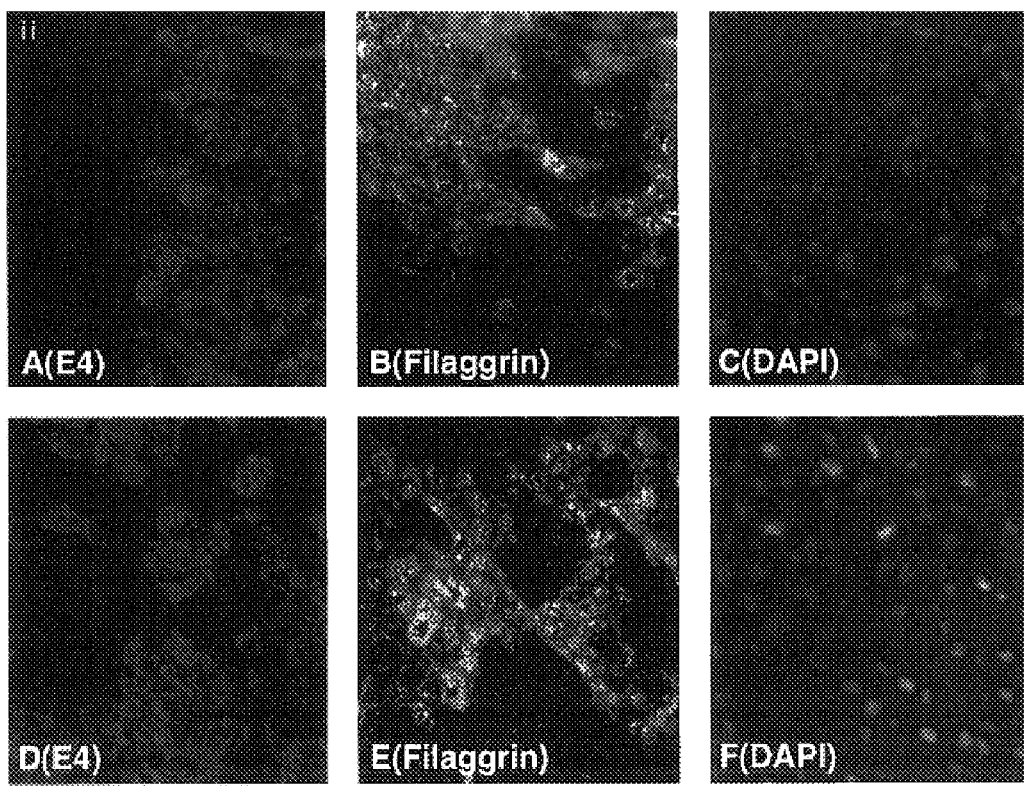
FIGS. 6(i) (A–F) show the results of staining, for HPV16 E4, HPV1 E4, HPV63 E4, differentiation specific mucosal keratins or cutaneous keratins, and DAPI counter stain, in a HPV16-induced CIN I, an HPV-1-induced verruca, and HPV63-induced wart.
Figure 6:
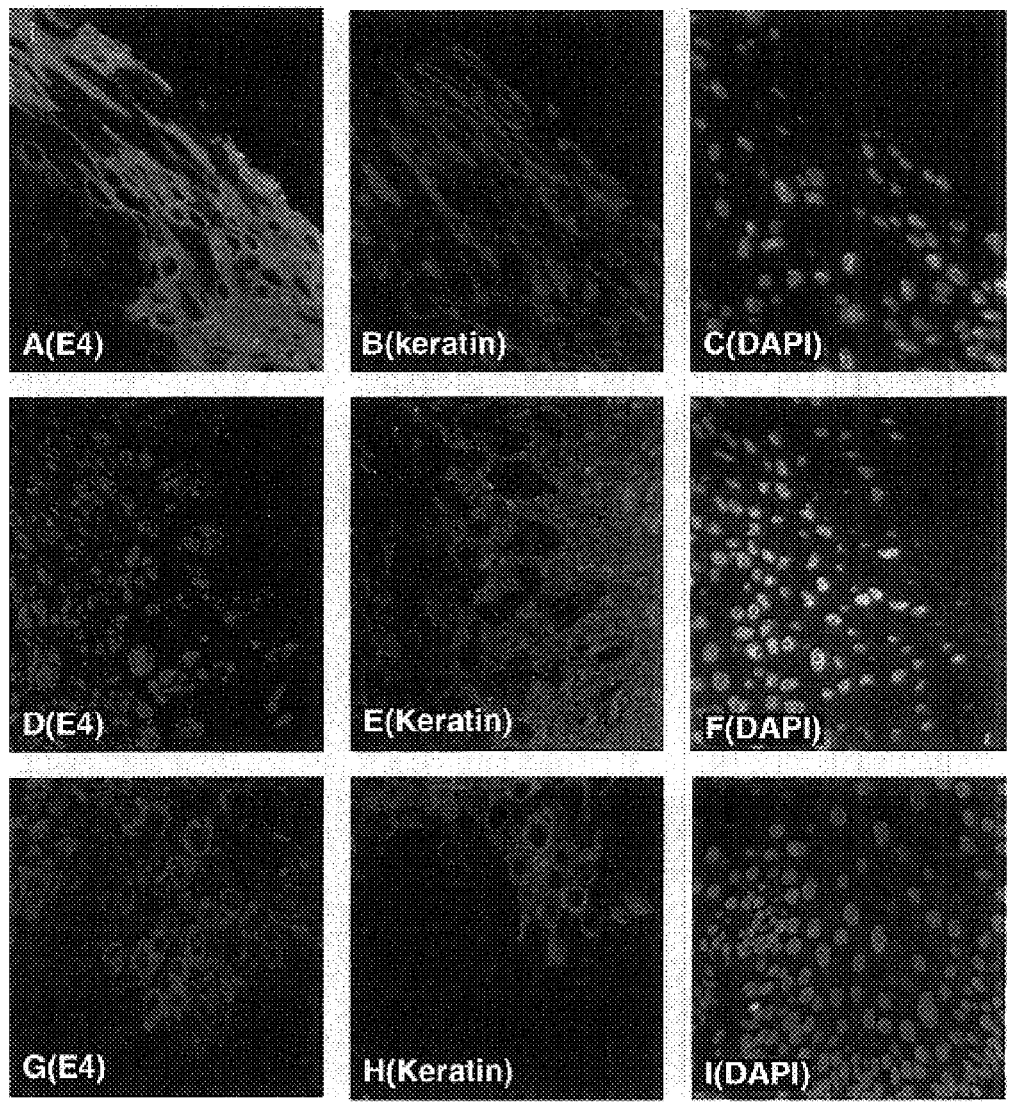
FIGS. 6(ii) (A–I) show the results of staining for HPV16 E4, HPV1 E4, HPV63 E4, filaggrin, and DAPI counter stain, in a HPV16-induced CIN I, an HPV-1-induced verruca, and an HPV63-induced wart FIGS. 7(A–D) show the association of HPV16 E4 proteins with perinuclear bundles and filamentous structures in vivo.

FIG. 6 illustrates that productive infection interferes with normal epithelial terminal differentiation. in low grade HPV16 lesions and in benign cutaneous warts. FIG. 6(i) (keratin expression) shows triple staining using the HPV16 E4 Fabs TVG405/TVG406 (FIG. 6(i)A), HPV 1 E4 monoclonals 4.37/9.95 (D), and HPV63 E4 polyclonal antibodies (G), in conjunction with antibodies to the differentiation-specific mucosal keratins 4 and 13 (B) or cutaneous keratins 1 and 10 (E, H). FIGS. 6(i) C, F and I show the DAPI counter stain. A, B and C represent a section through a HPV16-induced CIN I. D, E and F show a section through the edge of an HPV1-induced verruca, while FIGS. 6(i) G, H and I show a section through an HPV63-induced wart. In HPV16 and HPV1-induced lesions, differentiation-specific keratins are less apparent in E4-positive cells than in neighbouring cells (A, B, D, E) although this is not the case with HPV63 (G, H). Nuclear degeneration (visualised by DAPI counter staining) is retarded in E4-expressing cells (A, C, D, F). Magnification is 200×.

FIG. 6(ii) relates to filaggrin expression. The figure shows triple staining, as described above, except that FIGS. 6(ii) B and E show filaggrin staining. E4 staining is shown in FIGS. 6(ii) A and D, and DAPI counter staining is shown in FIGS. 6(ii) C and F. A, B and C represent the edge of an HPV63-induced wart where normal skin (left hand side of figure) meets the benign tumour (right hand side of figure). D, E and F show the granular layer of an HPV1-induced wart. E4-positive cells do not express detectable levels of the differentiation-specific marker filaggrin, and show marked nuclear preservation when compared to neighbouring uninfected or non-permissive cells. Magnification is 200×.

The Intracellular Distribution of the HPV16 E4 Proteins is Distinct from the Distribution of E4 in Cutaneous Lesions Caused by HPV1 and HPV63.

The E1^E4 protein of HPV1 is predominantly cytoplasmic and assembles into inclusions that coalesce and increase in size as the cell migrates towards the surface of the skin. The E1^E4 protein of HPV63 is found to have a fibrous and granular distribution. By contrast, HPV16 E4 had a filamentous and perinuclear distribution in cells of the lower epidermal layers (FIG. 7), and assembled into prominent structures only in the more differentiated cell layers. These 'inclusions' are always found singly per cell (c.f. multiple inclusions found in most cutaneous lesions), are located adjacent to the nucleus, and are nearly always detected on the side of the nucleus closest to the surface of the epidermis. Although similar in appearance to the E4/intermediate filament bundles which form after expression of the HPV16 E1^E4 protein in epithelial cells in vitro, we have not detected the presence of keratins in these structures in vivo. Antibodies to the very N-terminus of HPV16 E1^E4 stained the structures much less readily than antibodies to C-terminal epitopes (TVG 404, TVG405, TVG406) suggesting that the N-terminal region maybe either hidden or lost.

Figure 7:
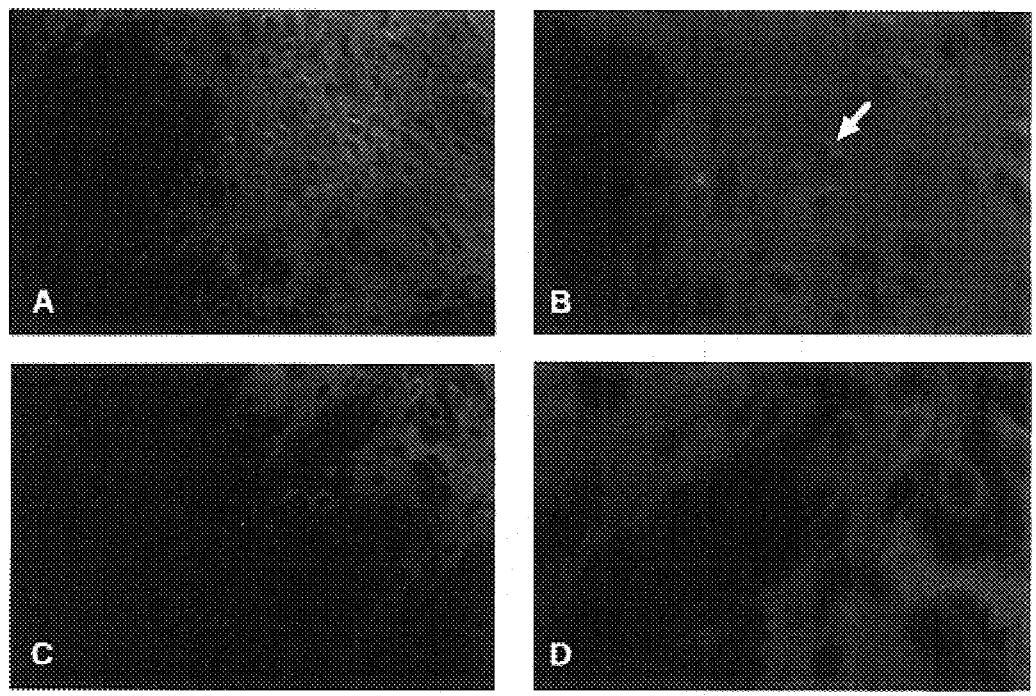

FIG. 7 shows the association of the HPV16 E4 proteins with perinuclear bundles and filamentous structure in vivo, in particular the detection of HPV16 E4 proteins in the upper layers (FIGS. 7A, B) and lower layers (FIGS. 7C, D) of a HPV16 CIN I using a mixture of Fabs TVG405 and TVG406. In the upper layers E4 is diffuse throughout the cytoplasm but with a prominent perinuclear pattern. Concentration of E4 into perinuclear bundles (arrowed in FIG. 7B) is apparent in these cells. In the lower layers, E4 has a predominantly perinuclear and filamentous appearance (FIGS. 7C, D), but is not concentrated into perinuclear bundles. Magnification for FIGS. 7A and C is 200×; that for B and D is 400×.

Figure 8:
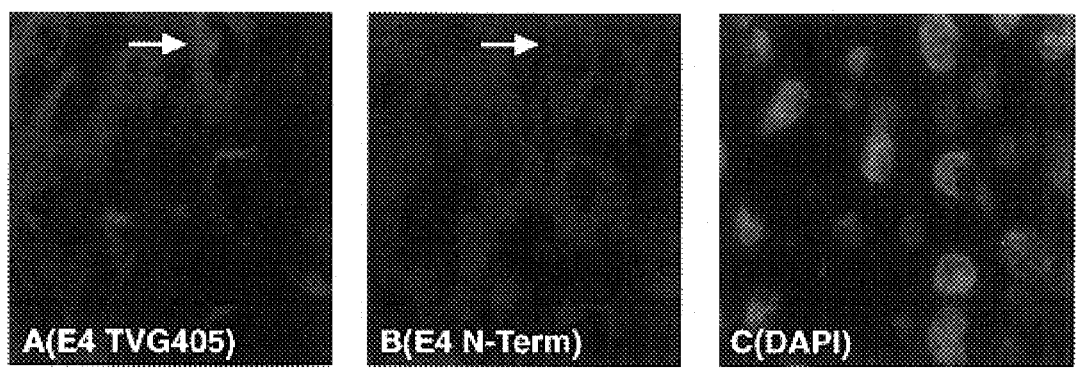
FIGS. 8(A–C) show staining in the upper layers of a HPV16 CIN for an epitope in the C-terminal half of the E4 protein, the N-terminal 12 amino acids of the HPV16 E1 E4 protein, or DAPI.

Confocal imaging revealed the N-terminal antibodies to localise primarily to the edge of the E4 structures while anti C-terminal staining is strongest in the centre (data not shown). When compared to the distribution seen with TVG405 and TVG406, the anti N-terminal reagent revealed HPV16 E1^E4 to have a more diffuse distribution in the cell (FIG. 8). No significant difference is apparent between the staining pattern of TVG405, 406, 407 and the C-terminal antibody.

FIG. 8 provides evidence for processing of the HPV16 E4 proteins in vivo and shows triple staining in the upper layers of a HPV16 CIN using HPV16 E4 Fab TVG406 which recognises an epitope in the C-terminal half of the E4 protein (FIG. 8A), an antibody to the N-terminal 12 amino acids of the HPV16 E1^E4 protein (FIG. 8B) and DAPI (FIG. 8C). TVG402, 403, 404, 405 and 407 produced staining patterns that are not significantly different from that of TVG 406. Anti N-terminal antibodies did not effectively stain the perinuclear bundles (8B) which are evident with TVG406 (arrowed in 8A) suggesting that as in HPV1, different forms of the protein have different intracellular locations. Magnification is 400×.

EXAMPLE 6

Detection of HSV in Cells Isolated from Cervical Lesions

Slides suitable for imaging of cells derived from cervical smears stained using anti-E4 antibodies are prepared by the method set forth in U.S. Pat. No. 5,346,831. Cells are isolated from a patient according to conventional procedures and dissolved in 10 ml alcohol/saline buffer. The sample is prepared for centrifugation by disaggregating the clumps or clusters of cells in the sample vial by vortexing. After disaggregation, the sample is drained completely and layered over a density gradient in a 12 ml conical cube, wherein the density gradient is formed with a plasma expander material comprising 6% betastarch solution, and 0.9% physiological saline, also known by the tradename "Hespan" made by NPBI, Emmer-Compascuum, the Netherlands.

12 ml conical tubes containing density gradient and sample cells are placed into centrifuge buckets, balance and centrifuged for 5 minutes, at a force of about 600 G. The liquid is then aspirated down to the 5 ml mark on the conical tube. The centrifuge buckets are removed and the 12 ml conical tube centrifuged with remaining liquid for 10 minutes, at 800 G. The tubes are emptied of supernatant, tapping lightly 2 or 3 times at a 45 degree angle. The tubes now contain packed cells of varying volumes. Upon mixing to homogeneity, the pellets generally contain the same concentration of cells per unit volume of liquid.

50 µl of deionized $H_2O$ is added, and the sample mixed by syringing 5 times through a 0.042 inch tip. Upon completion of mixing, 150 µl of sample followed by 500 µl of deionized $H_2O$ is dispensed into a sedimentation vessel attached to a slide which has been conventionally coated with Poly-L lysine (1% Sigma). The transferred sample is allowed to settle within the vessel for approximately 10 minutes. The excess sample is aspirated off and the chamber rinsed with 2 ml deionized $H_2O$ two times (aspirating between each addition).

FITC-labelled Fabs are then applied to the cells according to known procedures and the binding visualised by fluorescence microscopy.

References

Andrews & DiMaio, (1993) *J. Virol.* 67, 7705–7710.
Barksdale & Baker (1995). *J. Virol* 69, 6553–6556.
Beyer-Finkler et al, (1990) *Med. Microbiol. Immunol.* 179, 185–192.
Breitburd et al, (1987) In "Cancer Cells 5", pp. 115–122. cold Spring Harbor Laboratory press. Cold Spring Harbor, N.Y.
Brown et al, (1994) *Virology* 201, 46–54.
Chow & Broker (1994), *Intervirology* 37, 150–158.
Chow et al, (1987) *J. Virol.* 61, 2581–2588.
Croissant et al, (1985) *Clin. Dermatol.* 3(4), 43–55.
Crum et al, (1990) *Virology* 178, 238–246.
Dietrich-Goetz et al. (1997) *Proc. Natl. Acad. Sci. USA* 94, 163–168.
Doorbar, J. (1996). The E4 proteins and their role in the viral life cycle. In "Papillomavirus Reviews: Current Research on Papillomaviruses" (C. Lacey, Ed.), pp. 31–38. Leeds Medical Information, Leeds University Press, Leeds.
Doorbar et al, (1989). *EMBO J.* 5(2), 355–362.
Doorbar et al, (1989). *Virology* 172, 51–62.
Doorbar et al, (1992). 187, 353–359.
Doorbar et al, (1991) *Nature* 352, 824–827.
Doorbar et al, (1988). *EMBO J.* 73, 825–833.
Doorbar & Gallimore (1987). *J. Virol* 61, 2793–2977.
Doorbar et al, (1996a). *Virology* 218, 114–126;
Doorbar & Myers (1996b). The E4 protein. In "Human Papillomairuses 1996" (G. Myers, H. Delius, J. Icenogel, H.-U. Bernard, C. Baker, A. Halpern, and C. Wheeler, Eds), Vol. III, pp. 58–80. Los Alamos National Laboratory, Los Alamos, N. Mex., USA.
Egawa (1994) *Brit. J. Dermatol.* 130, 158–166.
Egawa et al, (1993a). *Virology* 194, 51–62.
Egawa et al, (1993b). *Brit. J. Dermatol.* 128, 271–276.
Frattini et al, (1996). *Proc. Natl. Acad. Sci. USA.* 93(7), 3062–3067.
Furth & Baker (1991). *J. Virol.* 65, 5806–5812.
Furth et al, (1994). *Mol. Cell Biol.* 14(8), 5278–5289.
Grand et al, (1989). *Virology* 170, 201–213.
Green et al, (1982). *Cell* 28, 477–487.
Griffiths et al, (1994). *EMBO J.* 13, 3245–3260.
Hawkins et al, (1992). *J. Mol. Biol.* 226, 889–896.
Hudson et al, (1992). *Hybridoma* 11(3), 367–378.
Hummel et al, (1995). *J. Virol.* 69, 3381–3388.
Jareborg & Burnett (1991). *J. Gen. Virol.* 72, 2269–2274.
Johnson et al, (1991). *Analyt. Biochem.* 198, 268–277.
Kennedy et al, (1991). *J. Virol.* 65, 2093–2097.
Laimins (1993). The Biology of Human Papillomaviruses: From Warts to Cancer. *Infectious Agents and Disease* 2, 74–86.
Lambert (1991). *J. Virol.* 65, 3417–3420.
Low et al, (1996). *J. Mol. Biol.* 260(3), 359–368.
Marks et al, (1992). *Bio-technology* 10(7), 779–783.
McClean et al, (1990) *J. Clin. Pathol.* 43, 488–492.
Meyers et al, (1992). *Science* 257, 971–973.
Nissim et al, (1994). *EMBO J.* 13, 692–698.
Palefsky et al, (1991). *J. Clin. Invest.* 87, 2132–2141.
Pope et al, (1996). *Immunotechnology* 2(3), 209–217.
Pray et al, (1995). *Virology* 206, 679–685.
Roberts & Wientraub (1996). *Cell* 46, 741–752.
Roberts et al, (1994). *J. Virol* 68(10), 6432–6455.
Roberts et al, (1993). *Virology* 197, 176–187.
Rogel-Gaillard et al, (1992). *J. Virol.* 66(2), 816–823.
Rogel-Gaillard et al, (1993). *J. Invest. Dermatol.* 101, 843–851.
Schier et al, (1996). *J. Mol, Biol.* 263(4), 551–567.
Schneider (1994). *Intervirology* 37(34), 201–214.
Sherman & Schlegel (1996). *J Virol.* 70, 3269–3279.
Stoler et al, (1990). *J. Virol.* 64, 3310–3318.
Stoppler et al, (1996). *J. Virol.* 70,6987–6993.
Villiers de (1994) Human pathogenic papillomavirus types: an update. In "Human Pathogenic Papillomaviruses" (H. Zur Hausen, Ed). ppl 1–12. Springer-Verlag, New York.
Zheng et al, (1996). *J. Virol.* 70, 4691–4699.

---

The invention claimed is:

1. A method of diagnosing a precancerous lesion resulting from a mucosal papilloma virus infection in an organism, the method comprising detecting vegetative mucosal papilloma viral DNA replication in a sample of cells from said organism as indicated by mucosal papilloma virus-E4 protein expression, wherein the detection of said virus-E4 protein comprises the steps of:

contacting in vitro a sample of the organism's cells from the site of potential infection with a molecule that binds specifically to mucosal papilloma virus-E4 protein; and monitoring said binding, wherein specific binding by said molecule to mucosal papilloma virus-E4 protein indicates the presence of mucosal papilloma virus-E4 protein expression and the detection of vegetative mucosal papilloma viral DNA replication, thereby indicating a precancerous lesion resulting from a mucosal papilloma virus infection in an organism.

2. The method according to claim 1, wherein the organism is a mammal.

3. The method according to claim 2, wherein the organism is a human and the papilloma virus is human papilloma virus (HPV).

4. The method according to claim 2, wherein the site of potential infection is the cervix.

5. The method according to claim 3, wherein the human papilloma virus is selected from the group consisting of HPV types 16, 18, 33, 35, 45, 51, 52, 56, 58 and 61.

6. The method according to claim 1, further comprising determining the type(s) of HPV infection in the organism, said determination comprising the step of: contacting the cells with a molecule that binds specifically to a subset of HPV E4 proteins; and monitoring said binding.

7. The method according to claim 1, wherein the molecule capable of binding to the papilloma virus E4 protein is capable of binding within a hydrophilic region of the E4 sequence.

8. The method according to claim 7, wherein the hydrophilic region is the region which possesses the sequence RPIPKPSPWAPKKHRRLSSDQDSQTP (SEQ ID NO:4) in HPV16. or its homologue in other papilloma viruses.

9. The method according to claim 8, wherein the hydrophilic region is the region which possesses the sequence RPIPKPSPWAPKKHR in HPV16 (SEQ ID NO:167), or its homologue in other papilloma viruses.

10. The method according to claim 9, wherein the hydrophilic region is the region which possesses the sequence PKPSPWAPKKLH(R) (SEQ NO: 168) in HPV16, or its homologue in other papilloma viruses.

11. The method according to claim 1, wherein the molecule capable of binding to a papilloma virus E4 protein is an antibody or an antigen binding fragment thereof.

12. The method according to claim 3, wherein the site of potential infection is the cervix.

13. The method according to claim 2, further comprising determining the type(s) of HPV infection in the organism, said determination comprising the steps of: contacting the cells with a molecule that binds specifically to a subset of HPV E4 proteins; and monitoring said binding.

14. The method according to claim 3, further comprising determining the type(s) of HPV infection in the organism, said determination comprising the steps of: contacting the cells with a molecule that binds specifically to a subset of HPV E4 proteins; and monitoring said binding.

15. The method according to claim 4, further comprising determining the type(s) of HPV infection in the organism, said determination comprising the steps of: contacting the cells with a molecule that binds specifically to a subset of HPV E4 proteins; and monitoring said binding.

16. The method according to claim 5, further comprising determining the type(s) of HPV infection in the organism, said determination comprising the steps of: contacting the cells with a molecule that binds specifically to a subset of HPV E4 proteins; and monitoring said binding.

17. The method according to claim 12, further comprising determining the type(s) of HPV infection in the organism, said determination comprising the steps of: contacting the cells with a molecule that binds specifically to a subset of HPV E4 proteins; and monitoring said binding.

18. The method according to claim 2, wherein the molecule capable of binding to the papilloma virus E4 protein is capable of binding within a hydrophilic region of the E4 sequence.

19. The method according to claim 3, wherein the molecule capable of binding to the papilloma virus E4 protein is capable of binding within a hydrophilic region of the E4 sequence.

20. The method according to claim 4, wherein the molecule capable of binding to the papilloma virus E4 protein is capable of binding within a hydrophilic region of the E4 sequence.

21. The method according to claim 5, wherein the molecule capable of binding to the papilloma virus E4 protein is capable of binding within a hydrophilic region of the E4 sequence.

22. The method according to claim 6, wherein the molecule capable of binding to the papilloma virus E4 protein is capable of binding within a hydrophilic region of the E4 sequence.

23. The method according to claim 12, wherein the molecule capable of binding to the papilloma virus E4 protein is capable of binding within a hydrophilic region of the E4 sequence.

24. The method according to claim 13, wherein the molecule capable of binding to the papilloma virus E4 protein is capable of binding within a hydrophilic region of the E4 sequence.

25. The method according to claim 14, wherein the molecule capable of binding to the papilloma virus E4 protein is capable of binding within a hydrophilic region of the E4 sequence.

26. The method according to claim 15, wherein the molecule capable of binding to the papilloma virus E4 protein is capable of binding within a hydrophilic region of the E4 sequence.

27. The method according to claim 16, wherein the molecule capable of binding to the papilloma virus E4 protein is capable of binding within a hydrophilic region of the E4 sequence.

28. The method according to claim 17, wherein the molecule capable of binding to the papilloma virus E4 protein is capable of binding within a hydrophilic region of the E4 sequence.

29. The method according to claim 18, wherein the hydrophilic region is the region which possesses the sequence RPIPKPSPWAPKKHRRLSSDQDSQTP (SEQ ID NO:4) in HPV16. or its homologue in other papilloma viruses.

30. The method according to claim 29, wherein the hydrophilic region is the region which possesses the sequence RPIPKPSPWAPKKHR in HPV16 (SEQ ID NO:167), or its homologue in other papilloma viruses.

31. The method according to claim 30, wherein the hydrophilic region is the region which possesses the sequence PKPSPWAPKKH(R) (SEQ NO:168) in HPV16, or its homologue in other papilloma viruses.

32. The method according to claim 19, wherein the hydrophilic region is the region which possesses the sequence RPIPKPSPWAPKKHRRLSSDQDSQTP (SEQ ID NO:4) in HPV16. or its homologue in other papilloma viruses.

33. The method according to claim 32, wherein the hydrophilic region is the region which possesses the sequence RPIPKPSPWAPKKHR in HPV16 (SEQ ID NO:167), or its homologue in other papilloma viruses.

34. The method according to claim 33, wherein the hydrophilic region is the region which possesses the sequence PKPSPWAPKKH(R) (SEQ NO:168) in HPV16, or its homologue in other papilloma viruses.

35. The method according to claim 20, wherein the hydrophilic region is the region which possesses the sequence RPIPKPSPWAPKKHRRLSSDQDSQTP (SEQ ID NO:4) in HPV16. or its homologue in other papilloma viruses.

36. The method according to claim 35, wherein the hydrophilic region is the region which possesses the sequence RPIPKPSPWAPKKHR in HPV16 (SEQ ID NO:167), or its homologue in other papilloma viruses.

37. The method according to claim 36, wherein the hydrophilic region is the region which possesses the sequence PKPSPWAPKKH(R) (SEQ NO:168) in HPV16, or its homologue in other papilloma viruses.

38. The method according to claim 21, wherein the hydrophilic region is the region which possesses the sequence RPIPKPSPWAPKKHRRLSSDQDSQTP (SEQ ID NO:4) in HPV16. or its homologue in other papilloma viruses.

39. The method according to claim 38, wherein the hydrophilic region is the region which possesses the sequence RPIPKPSPWAPKKHR in HPV16 (SEQ ID NO:167), or its homologue in other papilloma viruses.

40. The method according to claim 39, wherein the hydrophilic region is the region which possesses the sequence PKPSPWAPKKH(R) (SEQ NO:168) in HPV16, or its homologue in other papilloma viruses.

41. The method according to claim 22, wherein the hydrophilic region is the region which possesses the sequence RPIPKPSPWAPKKHRRLSSDQDSQTP (SEQ ID NO:4) in HPV16. or its homologue in other papilloma viruses.

42. The method according to claim 41, wherein the hydrophilic region is the region which possesses the sequence RPIPKPSPWAPKKHR in HPV16 (SEQ ID NO:167), or its homologue in other papilloma viruses.

43. The method according to claim 42, wherein the hydrophilic region is the region which possesses the sequence PKPSPWAPKKH(R) (SEQ NO:168) in HPV16, or its homologue in other papilloma viruses.

44. The method according to claim 23, wherein the hydrophilic region is the region which possesses the sequence RPIPKPSPWAPKKHRRLSSDQDSQTP (SEQ ID NO:4) in HPV16. or its homologue in other papilloma viruses.

45. The method according to claim 44, wherein the hydrophilic region is the region which possesses the sequence RPIPKPSPWAPKKHR in HPV16 (SEQ ID NO:167), or its homologue in other papilloma viruses.

46. The method according to claim 45, wherein the hydrophilic region is the region which possesses the sequence PKPSPWAPKKH(R) (SEQ NO:168) in HPV16, or its homologue in other papilloma viruses.

47. The method according to claim 24, wherein the hydrophilic region is the region which possesses the sequence RPIPKPSPWAPKKHRRLSSDQDSQTP (SEQ ID NO:4) in HPV16. or its homologue in other papilloma viruses.

48. The method according to claim 47, wherein the hydrophilic region is the region which possesses the sequence RPIPKPSPWAPKKHR in HPV16 (SEQ ID NO:167), or its homologue in other papilloma viruses.

49. The method according to claim 48, wherein the hydrophilic region is the region which possesses the sequence PKPSPWAPKKH(R) (SEQ NO:168) in HPV16, or its homologue in other papilloma viruses.

50. The method according to claim 25, wherein the hydrophilic region is the region which possesses the sequence RPIPKPSPWAPKKHRRLSSDQDSQTP (SEQ ID NO:4) in HPV16. or its homologue in other papilloma viruses.

51. The method according to claim 50, wherein the hydrophilic region is the region which possesses the sequence RPIPKPSPWAPKKHR in HPV16 (SEQ ID NO:167), or its homologue in other papilloma viruses.

52. The method according to claim 51, wherein the hydrophilic region is the region which possesses the sequence PKPSPWAPKKH(R) (SEQ NO:168) in HPV 16, or its homologue in other papilloma viruses.

53. The method according to claim 26, wherein the hydrophilic region is the region which possesses the sequence RPIPKPSPWAPKKHRRLSSDQDSQTP (SEQ ID NO:4) in HPV16. or its homologue in other papilloma viruses.

54. The method according to claim 53, wherein the hydrophilic region is the region which possesses the sequence RPIPKPSPWAPKKHR in HPV16 (SEQ ID NO:167), or its homologue in other papilloma viruses.

55. The method according to claim 54, wherein the hydrophilic region is the region which possesses the sequence PKPSPWAPKKH(R) (SEQ NO:168) in HPV16, or its homologue in other papilloma viruses.

56. The method according to claim 27, wherein the hydrophilic region is the region which possesses the sequence RPIPKPSPWAPKKHRRLSSDQDSQTP (SEQ ID NO:4) in HPV16. or its homologue in other papilloma viruses.

57. The method according to claim 56, wherein the hydrophilic region is the region which possesses the sequence RPIPKPSPWAPKKHR in HPV16 (SEQ ID NO:167), or its homologue in other papilloma viruses.

58. The method according to claim 57, wherein the hydrophilic region is the region which possesses the sequence PKPSPWAPKKH(R) (SEQ NO:168) in HPV16, or its homologue in other papilloma viruses.

59. The method according to claim 28, wherein the hydrophilic region is the region which possesses the sequence RPIPKPSPWAPKKHRRLSSDQDSQTP (SEQ ID NO:4) in HPV16. or its homologue in other papilloma viruses.

60. The method according to claim 59, wherein the hydrophilic region is the region which possesses the sequence RPIPKPSPWAPKKHR in HPV16 (SEQ ID NO:167), or its homologue in other papilloma viruses.

61. The method according to claim 60, wherein the hydrophilic region is the region which possesses the sequence PKPSPWAPKKH(R) (SEQ NO:168) in HPV16, or its homologue in other papilloma viruses.

62. The method according to any one of claims 2–5, 8–11, 14, 20–23, 25, 31–42, and 46–48, wherein the molecule capable of binding to a papilloma virus E4 protein is an antibody or an antigen binding fragment thereof.

* * * * *